US007173102B2

(12) United States Patent
DeGrado et al.

(10) Patent No.: US 7,173,102 B2
(45) Date of Patent: Feb. 6, 2007

(54) FACIALLY AMPHIPHILIC POLYMERS AS ANTI-INFECTIVE AGENTS

(75) Inventors: William F. DeGrado, Moylan, PA (US); Gregory N. Tew, Amherst, MA (US); Michael L. Klein, Ocean City, NJ (US); Dahui Liu, Wynnewood, PA (US); Jing Yuan, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/471,028

(22) PCT Filed: Mar. 7, 2002

(86) PCT No.: PCT/US02/22043

§ 371 (c)(1),
(2), (4) Date: May 11, 2004

(87) PCT Pub. No.: WO02/100295

PCT Pub. Date: Dec. 19, 2002

(65) Prior Publication Data

US 2004/0185257 A1    Sep. 23, 2004

Related U.S. Application Data

(60) Provisional application No. 60/274,145, filed on Mar. 8, 2001.

(51) Int. Cl.
*C08G 18/00* (2006.01)
*C08G 63/00* (2006.01)
*C08G 69/02* (2006.01)
*C08G 71/02* (2006.01)

(52) U.S. Cl. .................. 528/322; 528/310; 528/190; 528/191; 528/192; 528/193; 528/272; 528/327; 428/59; 428/123; 428/357; 428/409; 428/543; 428/152; 428/153; 424/76.8; 424/78.08; 424/401; 424/402; 424/422; 424/423; 424/424; 424/443; 427/256

(58) Field of Classification Search ............ 528/322, 528/310, 190–193, 272, 44–45, 49, 327; 606/228; 428/59, 123, 152–153, 357, 409, 428/543; 424/76.8, 78.04, 401–402, 405, 424/422–424, 443; 604/358, 374, 360, 372; 427/256
See application file for complete search history.

(56) References Cited

U.S. PATENT DOCUMENTS 3,829,563 A    8/1974  Barry et al.
4,343,788 A    8/1982  Mustacich et al.
4,392,848 A    7/1983  Lucas et al.
5,071,648 A    12/1991 Rosenblatt
5,543,448 A *  8/1996  Laughner .............. 524/109
5,847,047 A    12/1998 Haynie
5,856,245 A    1/1999  Caldwell et al.
5,874,164 A    2/1999  Caldwell
5,912,116 A    6/1999  Caldwell
5,994,340 A    11/1999 Maiti et al.
6,034,129 A    3/2000  Mandeville, III et al.
6,040,251 A    3/2000  Caldwell
6,083,602 A    7/2000  Caldwell et al.
6,290,973 B1   9/2001  Hawkins et al.
6,399,629 B1   6/2002  Chamberland et al.
6,537,961 B1   3/2003  Koch

FOREIGN PATENT DOCUMENTS

| JP | 63-108019    | * | 5/1988 |
| JP | 2003-165805  | * | 6/2003 |
| JP | 2004-168802  | * | 6/2004 |
| JP | 2004-323688  | * | 11/2004 |
| WO | WO 90/04401  |   | 5/1990 |
| WO | WO 95/00547  |   | 1/1995 |
| WO | WO 97/29160  |   | 8/1997 |
| WO | WO 97/49413  |   | 12/1997 |
| WO | WO 98/17625 A1 |  | 4/1998 |
| WO | WO 00/37541 A1 |  | 6/2000 |

OTHER PUBLICATIONS

Appella, D.H., et al., "Formation of Short, Stable Helices in Aqueous Solution by β-Amino Acid Hexamers," *J. Am. Chem. Soc.* 121:2309-2310, American Chemical Society (1999).

Barron, A.E., and Zuckerman, R.N., "Bioinspired polymeric materials: in-between proteins and plastics," *Curr. Opin. Chem. Biol.* 3:681-687, Current Biology Ltd. (1999).

Bjørnholm, T., et al., "Self-Assembly of Regioregular, Amphiphilic Polythiophenes into Highly Ordered π-Stacked Conjugated Polymer Thin Films and Nanocircuits," *J. Am. Chem. Soc.* 120:7643-7644, American Chemical Society (1998).

(Continued)

*Primary Examiner*—Irina S. Zemel
(74) *Attorney, Agent, or Firm*—Sterne, Kessler, Goldstein & Fox P.L.L.C.

(57) ABSTRACT

Facially amphiphilic polymers and articles made therefrom having biocidal surfaces are disclosed. The polymers can inhibit the growth of microorganisms in contact with the surface or in areas adjacent to said biocidal surface. There is also disclosed a method to identify and optimize the facial amphiphilicity of polyamide, polyester, polyurea, polyurethane, polycarbonate and polyphenylene polymers. Utility as a contact disinfectant is disclosed.

45 Claims, 11 Drawing Sheets

OTHER PUBLICATIONS

Boman, H.G., Innate immunity and the normal microflora, *Immunol. Rev. 173*:5-16, Munksgaard International Publishers (Feb. 2000).

Brooks, B.R., et al., "CHARMM: A Program for Macromolecular Energy, Minimization, and Dynamics Calculations," *J. Comp. Chem. 4*:187-217, John Wiley & Sons (1983).

Car, R., and Parrinello, M., "Unified Approach for Molecular Dynamics and Density-Functional Theory," *Phys. Rev. Lett. 55*:2471-2474, American Physical Society (1985).

Chen, J., et al., "Development of Protegrins for the Treatment and Prevention of Oral Mucositis: Structure-Activity Relationships of Synthetic Protegrin Analogues," *Biopolymers 55*:88-98, Wiley Interscience (2000) (Published online Jul. 28, 2000).

Gellman, S.H., "Foldamers: A Manifesto," *Acc. Chem. Res. 31*:173-180, American Chemical Society (1998).

Gennaro, R., and Zanetti, M., "Structural Features and Biological Activities of the Cathelicidin-Derived Antimicrobial Peptides," *Biopolymers 55*:31-49, Wiley Interscience (2000) (Published online Jul. 28, 2000).

Hamuro, Y., et al., "Novel Folding Patterns in a Family of Oligoanthranilamides: Non-Peptide Oligomers That Form Extended Helical Secondary Structures," *J. Am. Chem. Soc. 119*:10587-10593, American Chemical Society (1997).

Hamuro, Y., et al., "De Novo Design of Antibacterial β-Peptides," *J. Am. Chem. Soc. 121*:12200-12201, American Chemical Society (1999).

Hancock, R.E.W., and Lehrer, R., "Cationic peptides: a new source of antibiotics," *Trends Biotechnol. 16*:82-88, Elsevier Science Publishers B.V. (1998).

Haynie, S.L., et al., "Antimicrobial Activities of Amphiphilic Peptides Covalently Bonded to a Water-Insoluble Resin," *Antimicrob. Agents Chemother. 39*:301-307, American Society For Microbiology (1995).

Houseman, B.T., and Mrksich, M., "The microenvironment of immobilized Arg-Gly-Asp peptides is an important determinant of cell adhesion," *Biomaterials 22*:943-955, Elsevier Science (May 2001).

Hsu, S-H., and Chen, W-C., "Improved cell adhesion by plasma-induced grafting of L-lactide onto polyurethane surface," *Biomaterials 21*:359-367, Elsevier Science (Feb. 2000).

Kelly, T.J., et al., "Emission Rates of Formaldehyde from Materials and Consumer Products Found in California Homes," *Environ. Sci. Technol. 33*:81-88, American Chemical Society (1999).

Kochendoerfer, G.G., et al., "Total Chemical Synthesis of the Integral Membrane Protein Influenza A Virus M2: Role of Its C-Terminal Domain in Tetramer Assembly," *Biochemistry 38*:11905-11913, American Chemical Society (1999).

Liu, D., and DeGrado, W.F., "De Novo Design, Synthesis, and Characterization of Antimicrobial β-Peptides," *J. Am Chem. Soc. 123*:7553-7559, American Chemical Society (2001) (Published online Jul. 17, 2001).

Margel, S., et al., "Peptide, protein, and cellular interactions with self-assembled monolayer model surfaces," *J. Biomed. Mater. Res. 27*:1463-1476, Wiley Interscience (1993).

Martin, M.G., and Siepmann, J.I., "Novel Configurational-Bias Monte Carlo Method for Branched Molecules. Transferable Potentials for Phase Equilibria. 2. United-Atom Description of Branched Alkanes," *J. Phys. Chem. B 103*:4508-4517, American Chemical Society (1999).

Massia, S.P., and Hubbell, J.A., "Covalent Surface Immobilization of Arg-Gly-Asp- and Tyr-Ile-Gly-Ser-Arg-Containing Peptides to Obtain Well-Defined Cell-Adhesive Substrates," *Anal. Biochem. 187*:292-301, Academic Press (1990).

Massia, S.P., and Hubbell, J.A., "An RGD Spacing of 440 nm Is Sufficient for Integrin $\alpha_v\beta_3$-mediated Fibroblast Spreading and 140 nm for Focal Contact and Stress Fiber Formation," *J. Cell Biol. 114*:1089-1100. Rockefeller University Press (1991).

Massia, S.P., and Stark, J., "Immobilized RGD peptides on surface-grafted dextran promote biospecific cell attachment," *J. Biomed. Mater. Res. 56*:390-399, Wiley Interscience (2001) (Published online May 14, 2001).

Mrksich, M., and Whitesides, G.M., "Using Self-Assembled Monolayers to Understand the Interactions of Man-Made Surfaces with Proteins and Cells," *Annu. Rev. Biophys. Biomol. Struct. 25*:55-78, Annual Reviews (1996).

Mrksich, M., "Tailored substrates for studies of attached cell culture," *Cell. Mol. Life Sci. 54*:653-662, Birkhauser Verlag (1998).

Muir, T.W., et al., "Protein Synthesis by Chemical Ligation of Unprotected Peptides in Aqueous Solution," *Methods Enzymol. 289*:266-298, Academic Press (1997).

Nelson, J.C., et al., "Solvophobically Driven Folding of Nonbiological Oligomers," *Science 277*:1793-1796, American Association for the Advancement of Science (1997).

Oren, Z., and Shai, Y., "Mode of Action of Linear Amphipathic α-Helical Antimicrobial Peptides," *Biopolymers 47*:451-463, Wiley Interscience (1998).

Piskin, E., "Plasma processing of biomaterials," *J. Biomater. Sci. Polymer Ed. 4*:45-60, VSP (1992).

Prince, R.B., et al., "Twist Sense Bias Induced by Chiral Side Chains in Helically Folded Oligomers," *Angew. Chem. Int. Ed. 39*:228-230, Academic Press (Jan. 2000).

Röthlisberger, U., et al., "The torsional potential of perfluoro n-alkanes: A density functional study," *J. Chem. Phys. 104*:3692-3700, American Institute of Physics (1996).

Samson, N., et al., "Relationships Between Synthesis and Mechanical Properties of New Polyurea Materials," *J. Appl. Polym. Sci. 65*:2265-2280 Wiley (1997).

Scherf, U., "Oligo- and Polyarylenes, Oligo- and Polyarylenevinylenes," *Top. Curr. Chem. 201*:163-222, Springer-Verlag (1999).

Seebach, D, and Matthews, J.L., "β-Peptides: a surprise at every turn," *Chem. Commun. 21*:2015-2022, Chemical Society (1997).

Sekaran, G., et al., "Physicochemical and Thermal Properties of Phenol-Formaldehyde-Modified Polyphenol Impregnate," *J. Applied Polymer Sci. 81*:1567-1571, Wiley (Aug. 2001) (Published online May 30, 2001).

Siepmann, J.I., and Frenkel, D., "Configurational bias Monte Carlo: a new sampling scheme for flexible chains," *Mol. Phys. 75*:59-70, Taylor & Francis Ltd. (1992).

Sondossi, M., et al., "Factors Involved in Bactericidal Activities of Formaldehyde and Formaldehyde Condensate/Isothiazolone Mixtures," *Int. Biodeter. Biodegradation 32*:243-261, Elsevier Science (1993).

Stigers, K.D., et al., "Designed molecules that fold to mimic protein secondary structures," *Curr. Opin. Chem. Biol. 3*:714-723, Current Biology Ltd. (1999).

Tew, G.N., et al., "*De novo* design of biomimetic antimicrobial polymers," *Proc. Natl. Acad. Sci. USA 99*:5110-5114, National Academy of Sciences (Apr. 2002).

Tew, G.N., et al., "Simple Facially Amphiphilic Polymers as Peptide Mimics," *224th ACS National Meeting*, Boston, MA, Aug. 18-22, 2002, *Abstract 4*, American Chemical Society (Aug. 2002).

Tiller, J.C., et al., "Designing surfaces that kill bacteria on contact," *Proc. Natl. Acad. Sci. USA 98*:5981-5985, National Academy of Sciences (May 2001).

Vlugt, T.J.H., et al., "Improving the efficiency of the configurational-bias Monte Carlo algorithm," *Mol. Phys. 94*:727-733, Taylor & Francis Ltd. (1998).

Wick, C.D., et al., "Transferable Potentials for Phase Equilibria. 4. United-Atom Description of Linear and Branched Alkenes and Alkylbenzenes," *J. Phys. Chem. B 104*:8008-8016, American Institute of Physics (Aug. 2000) (Published online Aug. 1, 2000).

Woo, G.L.Y., et al., "Synthesis and characterization of a novel biodegradable antimicrobial polymer," *Biomaterials 21*:1235-1246, Elsevier Science (Jun. 2000).

Yamaguchi, I., et al., "Synthesis of polyurea rotaxanes using a cyclodextrin complex of α,ω-diamine," *Polym. Bull. 44*:247-253, Springer-Verlag (Apr. 2000).

U.S. Appl. No. 10/471,029, DeGrado et al., U.S. National Phase of-International Application No. PCT/US02/06899, filing date Mar. 7, 2002, published as WIPO Publication No. WO 02/072007 on Sep. 19, 2002.

U.S. Appl. No. 10/801,951, DeGrado et al., filed Mar. 17, 2004 (Not Published).

U.S. Appl. No. 10/446,171, Doerksen et al,, filed May 28, 2003.

Dialog File 351, Accession No. 11931138, English language abstract of WO 98/17625 A1.

* cited by examiner

P = polar group  N = nonpolar group

| | | | Antimicrobial Activity MIC (µg/mL)[1] | | | Hemolytic Activity HC$_{50}$ (µg/mL) |
|---|---|---|---|---|---|---|
| R | X | n | E. c. | K. p. | B. s. | |
| CH$_2$CH(CH$_3$)$_2$ | (CH$_2$)$_2$NHC(=NH)NH$_2$ | 4 | 20 | 50 | 6 | 200 |
| | | 5 | 20 | 25 | 6 | 200 |
| | (CH$_2$)$_5$NH$_2$ | 4 | 12 | 50 | 6 | 200 |
| | | 5 | 12 | 50 | 6 | 200 |
| | (CH$_2$)$_5$NHC(=NH)NH$_2$ | 4 | 12 | 50 | 12 | 35 |
| | | 5 | 12 | 50 | 12 | 8 |
| | (CH$_2$)$_2$NH$_2$ | 2 | >60 | 500 | 8 | >200 |
| | | 3 | >500 | >500 | 37 | >200 |
| | | 4 | ~30 | 63 | 8 | >200 |
| CH(CH$_3$)$_2$ | (CH$_2$)$_2$NH$_2$ | 4 | 100 | 500 | 100 | |
| | | 5 | 100 | 500 | 100 | |
| CH(CH$_3$)CH$_2$CH$_3$ | (CH$_2$)$_2$NH$_2$ | 4 | 500 | 500 | 20 | |
| | | 5 | 100 | 500 | 20 | |
| C$_6$H$_5$ | (CH$_2$)$_2$NH$_2$ | 4 | 500 | 500 | 100 | |
| | | 5 | 500 | >500 | 100 | |
| n-C$_4$H$_9$ | (CH$_2$)$_2$NH$_2$ | 4 | 500 | 500 | 500 | |
| | | 5 | 100 | 500 | 100 | |
| (CH$_2$)$_3$NHC(=NH)NH$_2$ | Me | 4 | >500 | 500 | 500 | |
| | | 5 | 500 | 500 | 500 | |
| (CH$_2$)$_3$NHC(=NH)NH$_2$ | iso-pentyl | 4 | 100 | 100 | 6 | 4 |
| | | 5 | 100 | 100 | 12 | 4 |
| (CH$_2$)$_4$NH$_2$ | | 2 | >500 | >500 | 25 | |
| | | 4 | 63 | 63 | <5 | |

[1] E.c. *Escherichia coli* D31; K.p. *Klebsiella pneumoniae* 10; B.s. *Bacillus subtilis*

*Figure 9*

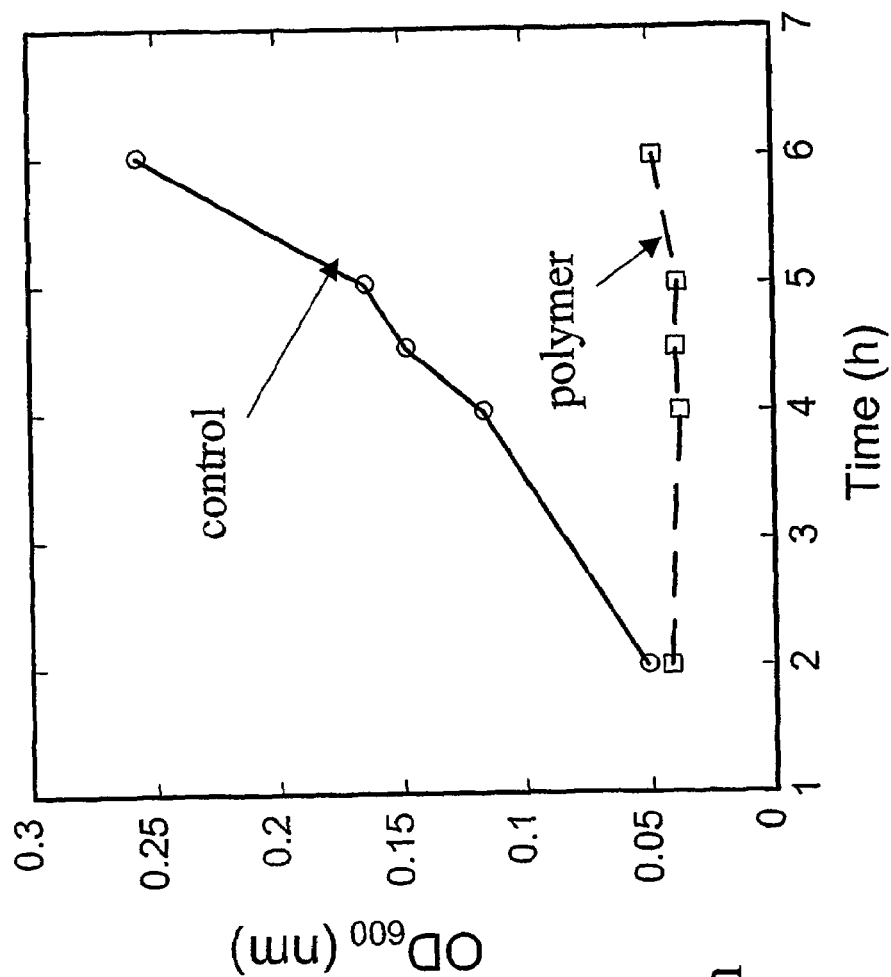
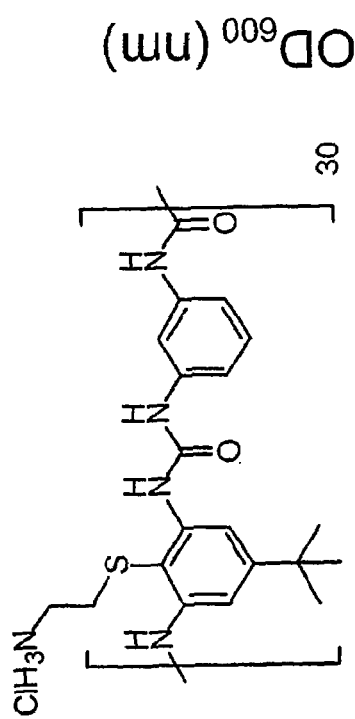
MIC = 25 µg/ml polyurea
MIC = 5 µg/ml magainin
*Figure 11*

FACIALLY AMPHIPHILIC POLYMERS AS ANTI-INFECTIVE AGENTS

REFERENCE TO PREVIOUS APPLICATIONS

This application claims priority to U.S. Provisional Patent Application Ser. No. 60/274,145 filed Mar. 8, 2001.

GOVERNMENT SUPPORT

This invention was supported in part by funding from the U.S. Government (NSF Grant DMR00-79909) and the U.S. Government may therefore have certain rights in the invention.

FIELD OF THE INVENTION

The present invention relates to the design and synthesis of facially amphiphilic polymeric compounds with microbiocidal properties that can be coated on or incorporated into materials and methods to design the same. The present invention further relates to methods to identify and design facially amphiphilic polymers and methods to prevent or limit microbial growth.

BACKGROUND OF THE INVENTION

Amphiphilic molecules exhibit distinct regions of polar and nonpolar character. These regions can result from substitution of hydrophobic and hydrophilic substituents into specific and distinct regions of conformationally defined molecules. Alternately a conformationally flexible molecule or macromolecule can adopt an ordered structure in which the hydrophobic and hydrophilic substituents on the molecule segregate to different areas or faces of the molecule. Commonly occurring amphiphilic molecules include surfactants, soaps, detergents, peptides, proteins and copolymers. These molecules have the capacity to self-assemble in appropriate solvents or at interfaces to form a variety of amphiphilic structures. The size and shape of these structures varies with the specific composition of the amphiphilic molecule and solvent conditions such as pH, ionic strength and temperature.

Amphiphilic peptides with unique broad-spectrum antimicrobial properties have been isolated from a variety of natural sources including plants, frogs, moths, silk worms, pigs and humans (H. G. Boman *Immunol Rev.* 2000 173: 5–16; R. E. Hancock and R. Lehrer, *Trends Biotechnol.* 1998 16:82–88). These compounds include the magainin 1 (1) and dermaseptin S1 (2) isolated from the skin of frogs and the cecropin A (3) isolated from the *cecropia* moth. These naturally occurring compounds have broad-spectrum anti-bacterial activity and they do not appear prone to the development of bacterial resistance. These compounds are relatively low molecular weight peptides that have a propensity to adopt α-helical conformation in hydrophobic media or near a hydrophobic surface and as a result are facially amphiphilic (i.e., one-third to two-thirds of the cylinder generated by the helical peptide has hydrophobic side chains while the

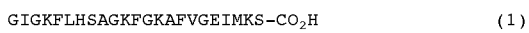

remainder has hydrophilic side chains. These hydrophilic side chains are primarily positively-charged at neutral pH. Hydrophobic amino acids compose 40–60% of the total number of residues in most anti-microbial peptides. The selectivity of the amphiphilic peptides (e.g. for bacteria vs. human erythrocytes) depends on the overall hydrophobicity. The biological activity of thee compounds depend on the ratio of charged (c) to hydrophobic (h) residues. When the ratio is varied from 1:1 (c:h) to 1:2 (c:h) peptides with more hydrophobic residues tend to be more active toward erythrocyte membranes. The physiochemical properties rather than the presence of particular amino acids or the tertiary structure of the side chains. Related peptides have been isolated from mammals and these anti-microbial peptides have been suggested to be an important component of the innate immune response. (Gennaro, R. et al. *Biopoylmers (Peptide Science)* 2000, 55, 31).

These observations recently have been extended to peptides (β-peptides) comprised of β-amino acids. These non-natural polypeptide mimetics also are capable of adopting stable α-helical and β-sheet structures although the precise geometries of these structure are different form those generated by α-amino acid oligomers. However, appropriate positioning of hydrophobic and hydrophilic residues results in amphiphilic conformations with similar antimicrobial properties. This further confirms the importance of repeating periodicity of hydrophobic and hydrophilic groups vis-à-vis the precise amino acid sequence in producing facial amphiphilic antimicrobial compounds. (D. Seebach and J. L. Matthews, *Chem Commun.* 1997 2105; Hamuro, Y., Schneider, J. P., DeGrado, W. F., *J. Am. Chem. Soc.* 1999, 121, 12200–12201; D. H. Appella et al., *J. Am. Chem. Soc.,* 1999 121, 2309).

Secondary structures other than helices may also give rise to amphiphilic compounds. The protegrins (4) are a related series of anti-microbial peptides. (J. Chen et al., *Biopolymers (Peptide Science)*, 2000 55 88) The presence of a pair of disulfide bonds between $Cys^6–Cys^{15}$ and $Cys^8–Cys^{13}$ results in a monomeric amphiphilic anti-parallel β-sheet formed by the chain termini and linked by a β-turn. The amphiphilic β-sheet conformation is essential for anti-microbial activity against both gram-positive and gram-negative bacteria.

The data related to anti-microbial peptides suggests that facial amphiphilicity, the alignment of polar (hydrophilic) and nonpolar (hydrophobic) side chains on opposite faces of a secondary structural element formed by the peptide backbone, and not amino acid sequence, any particular secondary/tertiary structure, chirality or receptor specificity is responsible for their biological activity.

Suitably substituted polymers which lack polyamide linkages also are capable of adopting amphiphilic conformations. Solid phase chemistry technology was utilized to synthesize a class of meta substituted phenylacetylenes that fold into helical structures in appropriate solvents (J. C. Nelson et al., *Science* 1997 277:1793–96; R. B. Prince et al., *Angew. Chem. Int. Ed.* 2000 39:228–231). These molecules contain an all hydrocarbon backbone with ethylene oxide side chains such that when exposed to a polar solvent (acetonitrile), the backbone would collapse to minimize its contact with this polar solvent. As a result of the meta substitution, the preferred folded conformation is helical. This helical folding is attributed to a "solvophobic" energy term; although, the importance of favorable π—π aromatic interactions in the folded state are also likely to be important. Furthermore, addition of a less polar solvent ($CHCl_3$)

results in an unfolding of the helical structure demonstrating that this folding is reversible.

Regioregular polythiophenes (5 and 6) have been shown to adopt amphiphilic conformations in highly ordered π-stacked arrays with hydrophobic side chains on one side of the array and hydrophilic side chains on the other side. These polymers form thin films useful in the construction of nanocircuits. (Bjørnholm et al., *J. Am. Chem. Soc.,* 1998 120, 7643) These materials would be facially amphiphilic as defined herein; however, no biological properties have reported for these compounds.

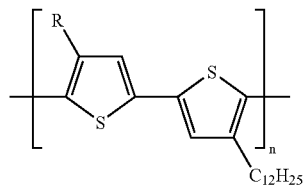

5: R = CH$_2$CO$_2^-$NMe$_4^+$
6: R = (CH$_2$CH$_2$O)$_3$Me

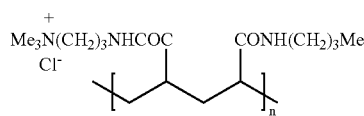

7

Antimicrobial peptides have been incorporated onto surfaces or bulk materials, with some retention of antimicrobial properties. Haynie and co-workers at DuPont have investigated the activity of Antibacterial peptides have been covalently attached to solid surfaces (S. L. Haynie et al., *Antimicrob Agents Chemother,* 1995 39:301–7; S. Margel et al., *J Biomed Mater Res,* 1993, 27:1463–76). A variety of natural and de novo designed peptides were synthesized and tested for activity while still attached to the solid support. The activity of the peptides decreased when attached to the solid support although the peptides retained their broad spectrum of activity. For example, a de novo designed peptide referred to as E14LKK has a MBC (minimum bactericidal activity) of 31 μg/ml in solution as opposed to 1.5 mg/ml when attached to a solid phase bead. The peptides were attached to the resin with a 2 to 6-carbon alkyl linker. The porosity of Pepsyn K, the resin used in the synthesis, is small (0.1 to 0.2 μm) compared to the bacteria, so the microbes may be unable to penetrate into the interior of the resin. Thus the great majority of the peptide would not be available for binding to cells. The antimicrobial activity did not arise from a soluble component; no leached or hydrolyzed peptide was observed and the soluble extracts were inactive. These studies indicate quite convincingly that antimicrobial peptides retain their activity even when attached to a solid support. However, there is a need to optimize the presentation of the peptides to increase their potency.

Other antimicrobial polymeric materials have been reported which contain chemical functionality known to be antimicrobial (J. C. Tiller et al., *Proc Natl Acad Sci U S A,* 2001 98:5981–85). A large portion of this work uses chemical functions such as alkylated pyridinium derivatives, which are known to be toxic to mammalian cells. The antibiotic ciprofloxacin has been grafted into a degradable polymer backbone (G. L. Y. Woo, et al., Biomaterials 2000 21:1235–1246). The activity of this material relies on cleavage of the active component from the polymer backbone.

Anti-infective vinyl copolymers, wherein monomers with hydrophobic and hydrophilic side chains have been randomly polymerized to produce polymers with amphiphilic properties, have also been described recently W. H. Mandeville III et al. (U.S. Pat. No. 6,034,129). These materials are produced by polymerization of hydrophobic and hydrophilic acrylate monomers. Alternately, the hydrophobic side chain is derived from a styrene derivative which is copolymerized with a hydrophilic acrylate monomer wherein an ionic group is linked to the carboxylic acid. These polymers, however, have relatively random arrangements of polar and nonpolar groups and are not facially amphiphilic as defined herein.

An alternative method to make amphiphilic polymers is to produce block copolymers comprised of hydrophobic blocks (A) and hydrophilic blocks (B), commonly polypropyleneoxy and polyethylenoxy segments respectively, into A-B, A-B-A or similar copolymers. These copolymers also are not facially amphiphilic as defined herein.

BRIEF DESCIRPTION OF FIGURES

BRIEF DESCRIPTION OF THE DRAWINGS

Specific embodiments of the invention have been chosen for the purpose of illustration and description but are not intended in any way to restrict the scope of the invention. These embodiments are shown in the accompanying drawings wherein:

In FIG. 9 there is shown antimicrobial data for polyamide and polyurea oligomers In FIG. 10 there is shown antimicrobial data for polyamide oligomers of general formula VII.

In FIG. 11 there is shown the time course for antibacterial activity of a polyurea oligomer.

SUMMARY OF THE INVENTION

Figure 1:
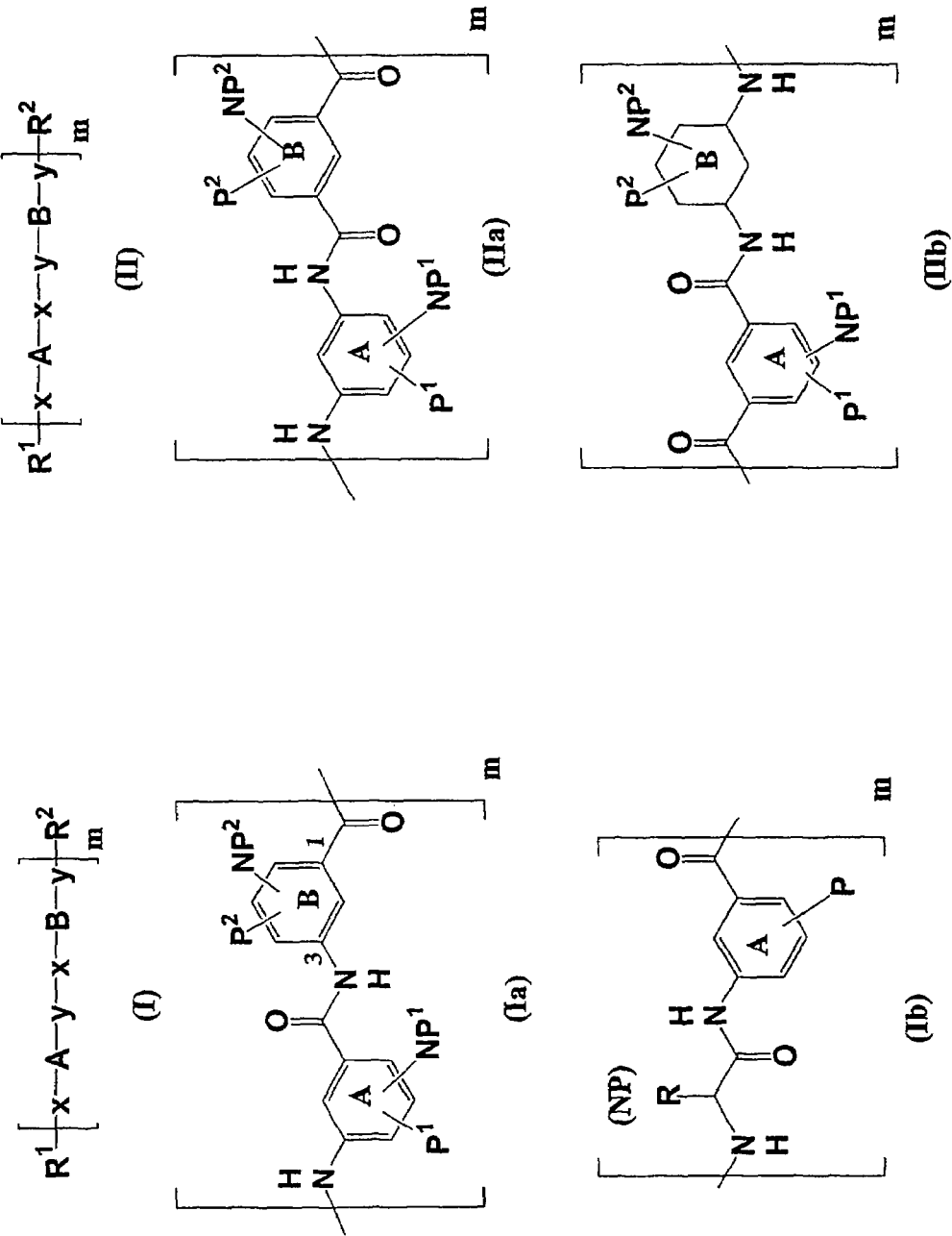
In FIG. 1 there is shown a cartoon that depicts the separation of hydrophobic and hydrophilic side chains onto opposite faces of the polymer backbone.

One object of the invention is to provide new polymeric compounds with anti-microbial properties which can be applied to or dispersed throughout devices, articles and surfaces and which are capable of killing microorganisms on contact, but leach into the environment more slowly than traditional small molecule anti-microbials. The polymeric materials may be deposited as a film on the surface of a substrate or may be dispersed

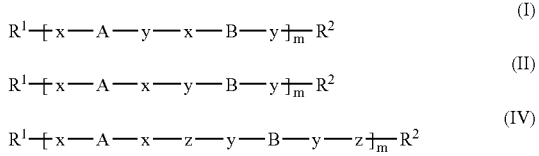

throughout a substrate to provide an anti-microbial surface. The polymeric materials of the present invention are anti-microbial polymers that are designed to possess amphiphilic properties in the presence of microbial cell walls and to disrupt the membrane and kill the organism. The polymeric materials are further designed to have low toxicity to mammalian cells.

The facially amphiphilic polymers of the present invention are polyamide or polyester compounds of formulae I and II wherein x is O, $NR^3$ or S, y is CO, CS or $SO_2$ and A and B are aromatic, heteroaromatic or aliphatic moieties appropriately substituted with polar and nonpolar groups; polyurea, polycarbamate, or polycarbonates compounds of formulae IV wherein x and y are O, $NR^3$ or S, z is CO, CS or $SO_2$ and A and B are aromatic, heteroaromatic or aliphatic moieties appropriately substituted with polar and nonpolar groups; and polyphenylene and heteroarylene compounds of formula V wherein is either a single bond, double bond, triple bond or absent and A and B are aromatic, heteroaromatic moieties appropriately substituted with polar and nonpolar groups. R, $R^1$ and $R^2$ are end groups appropriate for the specific polymer chain and their design is well know in the polymer art.

These facially amphiphilic polymers are capable of adopting repeating secondary structural motifs that allow for the segregation of polar and nonpolar regions of the molecule into different spatial regions. The anti-microbial polymers adopt amphiphilic conformations when placed in contact with the cell walls of microorganisms and the amphiphilic molecules are capable of disrupting essential cell wall functions resulting in the death of the microorganism.

The present invention further provides methods for killing microorganism on surfaces by disposing thereon a facially amphiphilic polymer. The method for making compositions incorporating the facially amphiphilic polymers includes providing a solution dispersion or suspension of the polymer and applying it to the surface. Alternately compositions can be prepared by incorporating the polymer into plastics that subsequently are molded, shaped or extruded into other articles. The optimal method to deliver the polymer will depend on several factors including the desired coating thickness and the nature and configuration of the substrate and the physical characteristics of the facially amphiphilic polymer.

The facially amphiphilic polymers of the present invention can have a substantial range in molecular weight. Facially amphiphilic molecules with molecular weights of about 0.8 kD to about 20 kD will be more prone to leach from the surface of the substrate. The facially amphiphilic polymer may be attached or immobilized on the substrate by any appropriate method including covalent bonding, ionic interaction, coulombic interaction, hydrogen bonding or cross-linking. The polymers of the present invention provide a surface-mediated microbiocide that only kills organisms in contact with the surface. Moreover the polymers of the present invention are stable and retain their bioactivity for extended periods of time and are nontoxic to birds, fish, mammals and other higher organisms.

The present invention further provides a computational technique to evaluate the energy of polymer conformations and identify polymers which have the capability of exhibiting amphiphilic behavior and aid in identifying optimal sites for substitution of polar and nonpolar substituents that confer amphiphilic properties.

DETAILED DESCRIPTION OF THE INVENTION

Microbial infections represent a serious continuing problem in human and animal health. While amphiphilic α and β-peptides exhibit potent antibacterial, they are, nevertheless, difficult and expensive to prepare in large quantities. Peptides are sensitive to enzymatic and chemical hydrolysis. Exposure to microbial pathogens can occur in a variety of ways. Most objects encountered daily have the potential for harboring infectious organisms and new compounds and approaches for controlling the growth of microbes are extremely valuable and have significant commercial potential. Antimicrobial peptides related to the magainins have desirable biological activities but their utility is limited. An object the present invention is to provide new stable antimicrobial polymers which are available from inexpensive and readily available monomers and which can be incorporated into, or on to, a wide variety of materials and can withstand chemical and enzymatic degradation.

In recent years, the design of non-biological polymers with well-defined secondary and tertiary structures (S. H. Gellman et al., *Acc. Chem. Res.* 1998 31:173–80; A. E. Barron and R. N. Zuckerman, *Curr. Opin. Chem. Biol.*, 1999 3:681–687; K. D. Stigers et al., *Curr. Opin. Chem. Biol.*, 1999 3:714–723) has become an active area of research. One reason for this interest is that for the first time, modern methods of solid phase organic chemistry (E. Atherton and R. C. Sheppard, *Solid Phase Peptide Synthesis A Practical Approach* IRL Press Oxford 1989) have allowed the synthesis of homodisperse, sequence-specific oligomers with molecular weights approaching 5,000 Daltons. The development of this new field of homodisperse sequence-specific oligomers promises to generate molecules with novel chemical and physical properties that will span the gap between polymer and protein science. Polymers are statistical mixtures of molecules typically composed of one to a few monomers. By contrast, peptides and proteins are molecules typically composed from >15 monomers with exact control over sequence, topology, and stereochemistry. These homodisperse sequence-specific oligomers represent molecules with features of both polymers and proteins.

Figure 7:
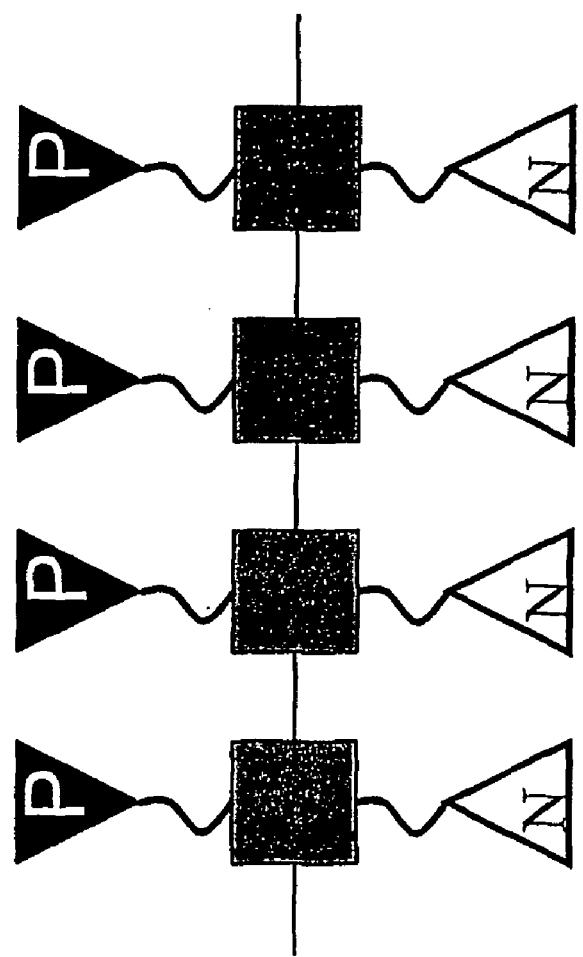
In FIG. 7 there is shown the synthesis of substituted salicylic and anthranilic acid monomers of XII and XIII.

Facially amphiphilic polymers can be homopolymers wherein one monomer is substituted with both a nonpolar and a polar substituent or copolymers wherein one monomer is substituted with a polar substituent and the other monomer is substituted with a nonpolar substituent. Since the antimicrobial activity arises from the amphiphilic character conferred by a periodic pattern of side chains rather than the precise spatial arrangement of side chains, other substitution patterns are also expected to produce facially amphiphilic polymers and they all are encompassed by the present invention. (see FIG. 7)

Polyamide and polyester homopolymers and copolymers of the present invention (FIG. 1) can be comprised solely of aromatic or heteroaromatic monomers or may include both aromatic and aliphatic monomers. One embodiment of the invention is a copolymer with aromatic monomers and α-amino acid monomers. The polyamides and polyesters can be constructed either by repetitively linking amino (or hydroxy) acid monomers (FIG. 1, I) or by alternating diamine (or dihydroxy) and dicarboxylic acid monomers (FIG. 1, II). While the majority of aromatic rings in the examples depicted in FIGS. 1 and 2 have a meta substitution pattern, one skilled in the art would immediately appreciate that equivalent polymers could be designed with an ortho or a para orientation and these modifications can alter the conformation and the physical properties of the resulting polymer. Furthermore although the copolymers in FIG. 1 Ia and IIa–IIc are depicted with one polar and one nonpolar substituent, other substitution patterns are equally plausible. The optimal substitution patterns are determined by the conformational properties of the polymer backbone.

Figure 2:
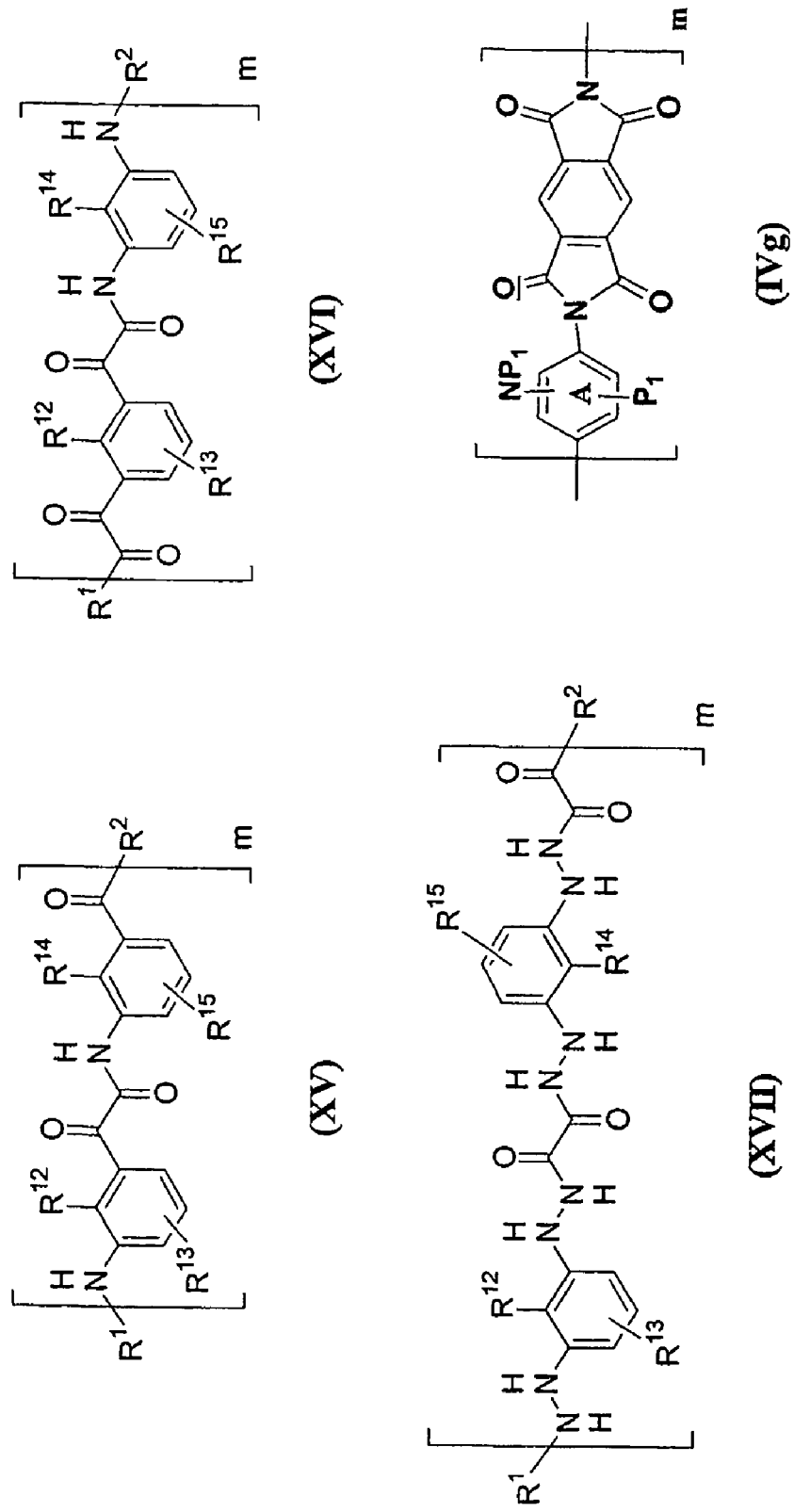
In FIG. 2 there is shown the general structure of a facially amphiphilic polyamide or polyester copolymer formulae I and II, representative monomer units for aromatic polyamides, Ia and IIa, the two representative monomer units for polyamides with both aromatic and aliphatic components, Ib and IIb.

While polyamides and polyesters are the most common occurring examples of the present invention, other functional groups can be incorporated into the polymer backbone with similar results. In particular, thioamides and thioesters are anticipated to have very similar properties. The distance between aromatic rings can significantly impact the geometrical pattern of the polymer and this distance can be altered by incorporating aliphatic chains of varying length (FIG. 1, IIc). Although IIc is depicted as a unsubstantiated alkylene chain, the alkylene chain can be optionally substituted or can comprise an amino acid, a dicarboxylic acid or a diamine. The distance between and the relative orientation of monomers also can altered by replacing the amide bond with a surrogate with additional atoms (FIG. 2, XV–XVII). Thus replacing the carbonyl group with a dicarbonyl alters the distance between the monomers and the propensity of dicarbonyl unit to adopt an anti arrangement of the two carbonyl moiety and alter the periodicity of the polymer. Pyromellitic anhydride (FIG. 2, IVg) represents still another alternative to simple amide linkages which can significant alter the conformation and physical properties of the copolymer (FIG. 1, IVb).

The synthetic processes can be modified to produce different ranges in molecular weight and the anti-microbial polymer of the present invention will have a molecular weight selected to impart physical and chemical properties optimized for the particular application being contemplated. Traditional polymer syntheses produce a product with a range of molecular weights. The polymer chemist will readily appreciate that the chain length of these polymers can be varied by techniques know in the polymer art. Polymers of the present invention can range in molecular weight from about 800 Daltons up to about 350 kiloDaltons. Advancements in solid-phase and solution phase synthesis of amino acid oligomers have made available techniques to prepare homogeneous polymers or oligomers with defined sequence and size and these techniques can be adapted to the present invention.

Figure 3:
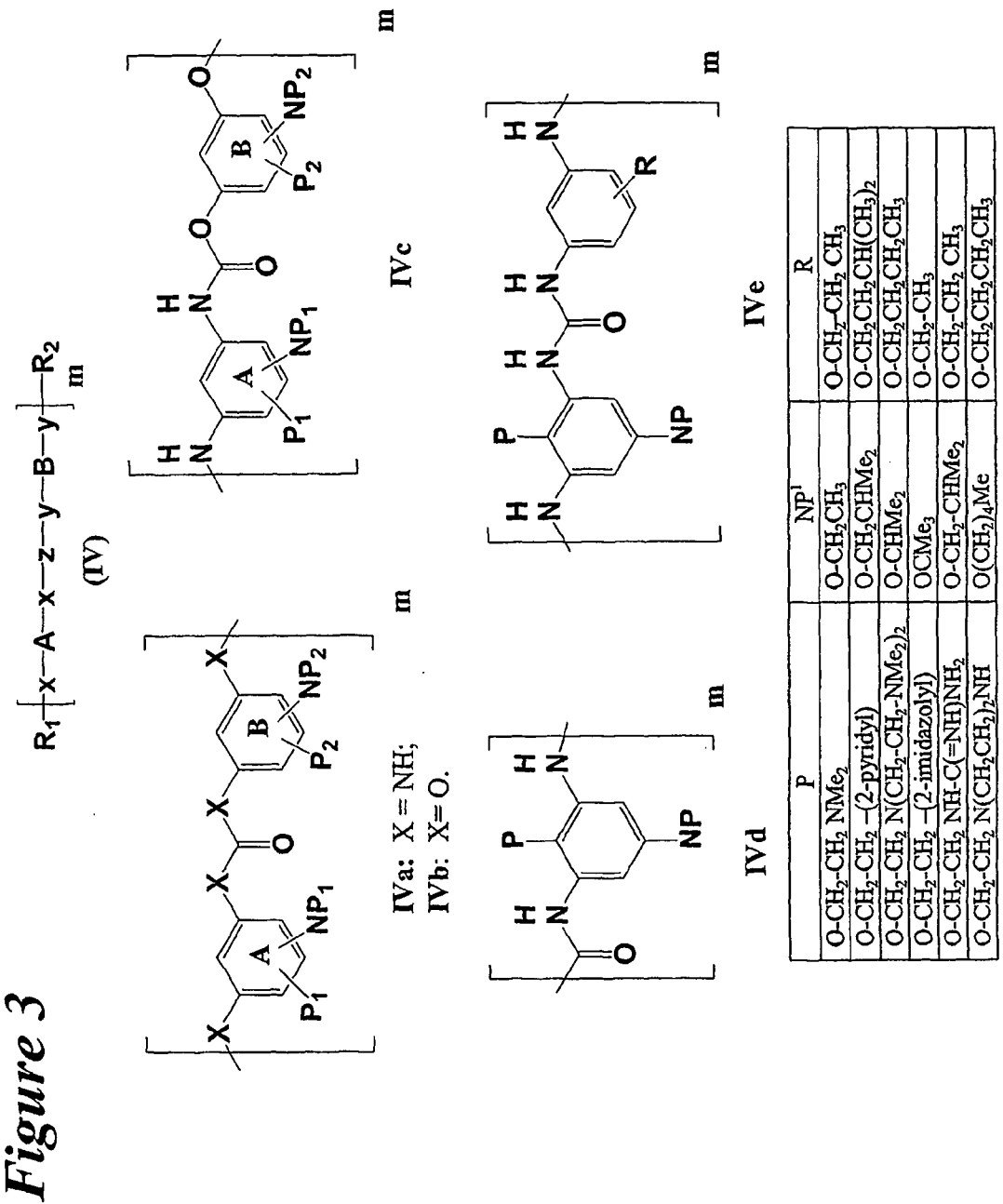
In FIG. 3 there is shown the general structure of polyamides with extended linking groups between the monomers.
Figure 4:
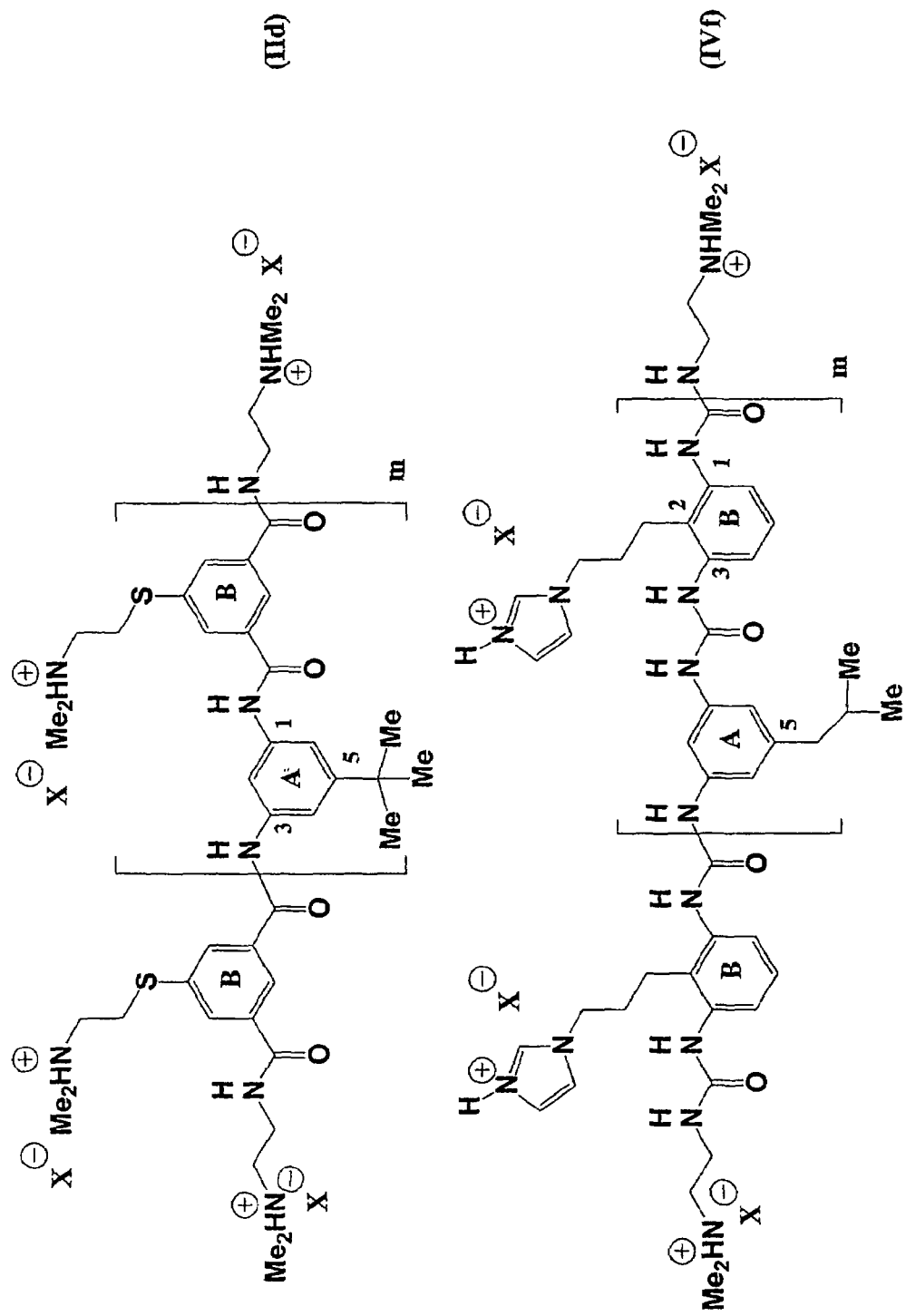
In FIG. 4 there is shown the general structure IV of a facially amphiphilic polyurea, polycarbonate and polyurethane copolymers and representative monomer units IVa, IVb and IVc, respectively. Examples of two typical polyurea monomers are exemplified in IVd and IVe.
Figure 5:
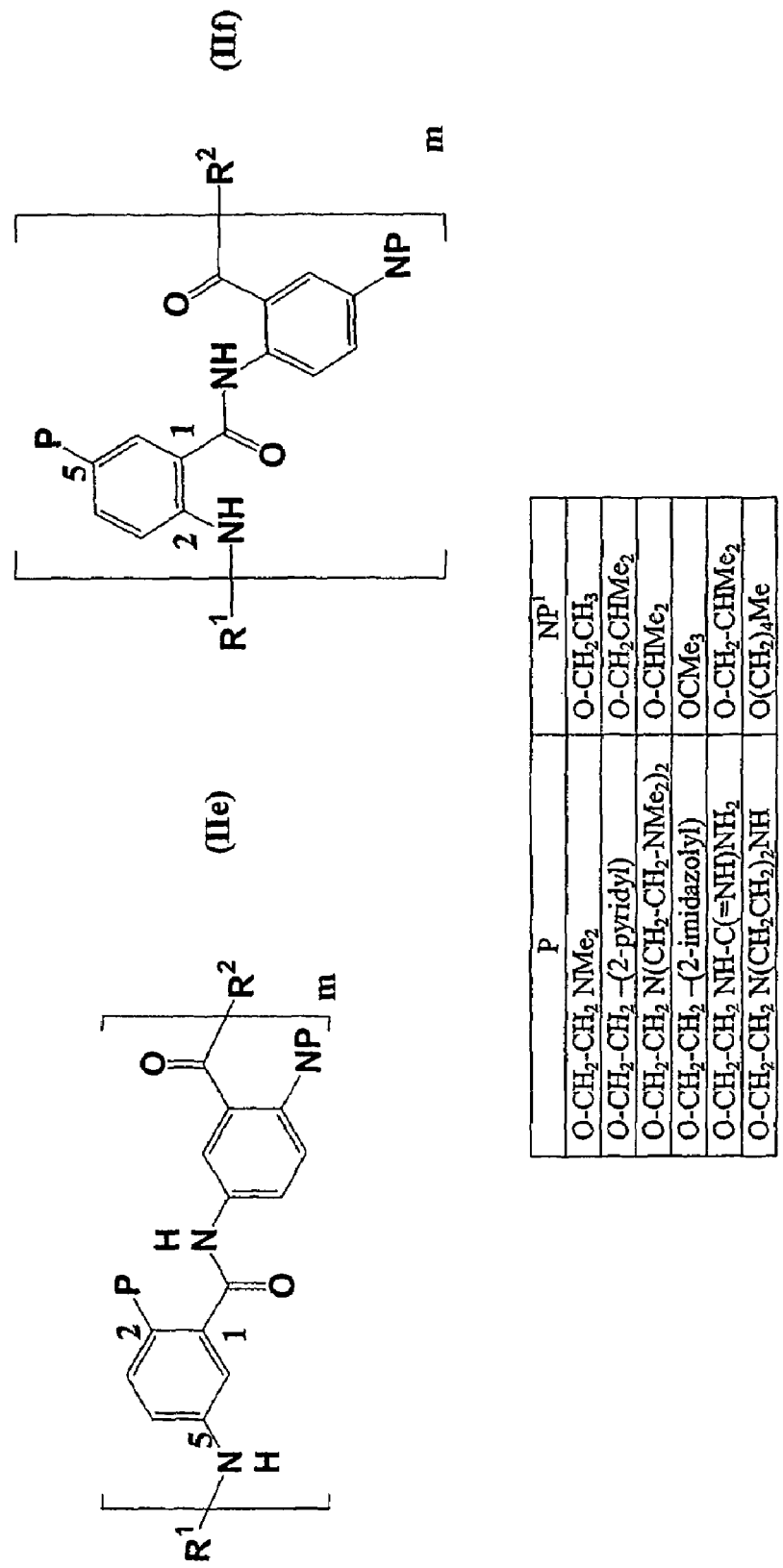
In FIG. 5 there is shown the complete structure of a facially amphiphilic polyamide IId and polyurethane IVf.

Polyureas (FIG. 3, IVa), polycarbonates (FIG. 3, IVb) or polyurethanes (FIG. 3, IVc) are carbonic acid derivatives and exhibit properties similar to polyamides (N. Samson et al. *J. Appl. Polym. Sci.* 65, 2265 (1997)). FIG. 3 IVd and IVe depict two different substitution patterns which can be utilized. Other substitution patterns are equally effective.

The polymer design process simply requires a structure in which the repeating sequence of monomers matches the secondary structure adopted by the backbone. Once the periodicity is observed, monomers substituted with polar and nonpolar groups monomers must be prepared and introduced to produce a cationic, amphiphilic secondary. Aromatic polyamides and ureas frequently have only a few torsional degrees of freedom per repeat (typically two or four). In this case the secondary structure adopted by these polymers is most likely planar with polar and nonpolar groups extended from opposite sides of the backbone. In some cases, the desired facial amphiphilicity can be achieved through a simple design principal.

Additional molecular features can be added to the macromolecular backbone to promote the desired secondary structure and disfavor other structures thereby combining elements of both positive and negative design. Conformational studies on biofoldamers (proteins and RNA), and early work with a variety of sequence-specific polymers, have shown that several elements are crucial in order for the polymers to adopt the desired folded conformation. Key elements include strong electrostatic interactions (i.e., intramolecular hydrogen bonding) between adjacent or more distant monomers and rigidification caused by the backbone torsions or by bulky functional groups. For example, the presence of multiple hydrogen bond donors and acceptors along the macromolecular backbone can lead to extensive intermolecular backbone interactions. Precise placement of well designed intramolecular interactions can stabilize desired secondary structures while at the same time blocking the backbone hydrogen bond donors which limits intermolecular aggregation problems. For example, in the polyurea and polyamide a thioether (FIG. 3, XIa–c) was positioned between the two aromatic nitrogens to form an internal hydrogen bond between the sulfur and urea function. This limits the torsional angle of the aromatic carbon-urea NH bond by forcing the NH group to be on the same side as the heteroatom, thereby helping to define the overall sheet-like secondary structure. The secondary structure for this backbone is predicted to be nearly planar. Similarly, the polyanthranilate polymer (XIII) is designed based on the finding of Hamuro and Hamilton (Y. Hamuro et al., *J. Am. Chem. Soc.* 1996 119:10587–93) that intramolecular hydrogen-bonding defines the secondary structure of this class of poly-arylamides.

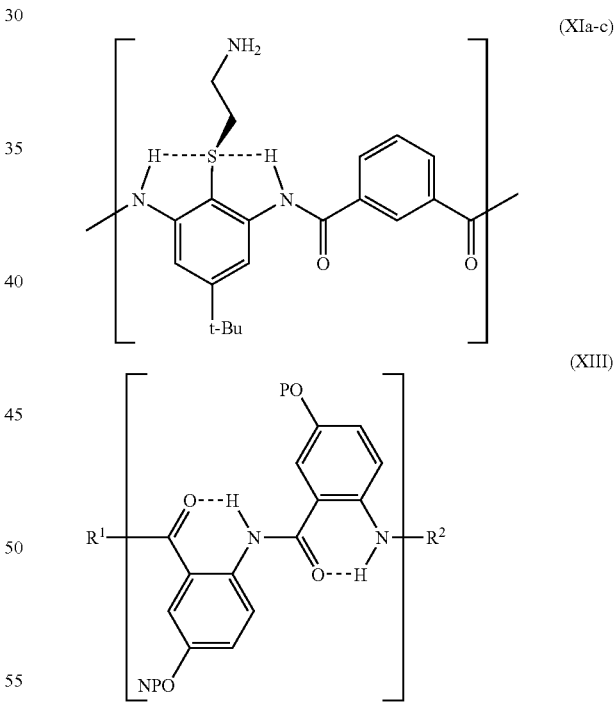

Magainin and the other naturally occurring antibacterial peptides exhibit considerable variation in their chain length, hydrophobicity and distribution of charges. These linear peptides do, however, contain positively charges amino acids and a large hydrophobic moment resulting in a high propensity to adopt α-helical conformations in a hydrophobic environment, e.g., a cell surface or a natural or synthetic membrane. (Z. Oren and Y. Shai Biopolymers (Peptide Science), 1998 47, 451–463.) The periodic distribution of hydrophobic and hydrophilic side chains in their amino acid sequences allows the segregation of the hydrophobic and hydrophilic side chains to opposite faces of the cylinder formed by the helix. The overall amphiphilicity, not the specific sequence, secondary structure or chirality, correlates best with anti-microbial activity. Thus it appears that any suitably amphiphilic material (not necessarily an α-helix or β-sheet) would have anti-microbial properties. The necessary condition for forming a facially amphiphilic structure is the molecule should have a repeating pattern of polar and nonpolar side chains whose periodicity is approximately the same as that of the secondary structure of interest.

The term "microorganism" as used herein includes bacteria, algae, fungi, yeast, mycoplasmids, parasites and protozoa.

The term "antimicrobial", "microbiocidal" or "biocidal" as used herein means that the materials inhibit, prevent, or destroy the growth or proliferation of microorganisms. This activity can be either bacteriocidal or bacteriostatic. The term "bacteriocidal" as used herein means the killing of microorganisms. The term "bacteriostatic" as used herein means inhibiting the growth of microorganisms which can be reversible under certain conditions.

The term "polymer" as used herein refers to a macromolecule comprising a plurality of repeating units or monomers. The term includes homopolymers, which are formed from a single type of monomers and copolymers that are formed from two or more different monomers. In copolymers the monomers may be distributed randomly (random copolymer), in alternating fashion (alternating copolymer) or in blocks (block copolymer). The polymers of the present invention are either homopolymers or alternating copolymers. The term "polymer" as used herein is intended to exclude proteins, peptides, polypeptides and other proteinaceous materials composed exclusively of α or β-amino acids. The term "oligomer" as used herein refers to a homogenous polymer with a defined sequence and molecular weight.

The term "polymer backbone" or "backbone" as used herein refers to that portion of the polymer which is a continuous chain comprising the bonds formed between monomers upon polymerization. The composition of the polymer backbone can be described in terms of the identity of the monomers from which it is formed without regard to the composition of branches, or side chains, off the polymer backbone.

The term "polymer side chain" or "side chain" refers to portions of the monomer which, following polymerization, forms an extension off the polymer backbone. In homopolymers all the polymer side chains are derived from the same monomer. A copolymer can comprise two or more distinct side chains from different monomers.

The term "alkyl" as used herein denotes a univalent saturated branched or straight hydrocarbon chain. Unless otherwise stated such chains contain from 1 to 18 carbon atoms. Representative of such alkyl groups are methyl, ethyl, propyl, iso-propyl, sec-butyl, tert-butyl, pentyl, neopentyl, iso-pentyl, hexyl, iso-hexyl, heptyl, octyl, nonyl, decyl, tridecyl, tetradecyl, hexadecyl octadecyl, and the like. When qualified by "lower" the alkyl group will contain from 1 to 6 carbon atoms. The term "cycloalkyl" as used herein denotes a univalent cyclic hydrocarbon chain. Representative groups are cyclopropyl, cyclobutyl, cyclohexyl, cyclopentyl and cyclohexyl.

The phrase "groups with chemically nonequivalent termini" refers to functional groups such as esters amides, sulfonamides and N-hydroxyoximes where reversing the orientation of the substituents, e.g. $R^1C(=O)OR^2$ vs. $R^1O(O=)CR^2$, produces unique chemical entities.

The term "basic heterocycle" as used herein denotes cyclic atomic array which includes a nitrogen atom that has a pKa greater than about 5 and that is protonated under physiological conditions. Representative of such basic heterocycles are pyridine, quinoline, imidazole, imidazoline, cyclic guanidines, pyrazole, pyrazoline, dihydropyrazo line, pyrrolidine, piperidine, piperazine, 4-alkylpiperazine, and derivatives thereof such as 2-aminopyridine, 4-amninopyridine, 2-aminoimidazoline, 4-aminoimidazoline or VII where $X^1$ is O, N, S or absent and i is 2 to 4.

(VII)

The term "amphiphilic" as used herein describes a three-dimensional structure having discrete hydrophobic and hydrophilic regions. An amphiphilic polymer requires the presence of both hydrophobic and hydrophilic elements along the polymer backbone. The presence of hydrophobic and hydrophilic groups is a necessary, but not sufficient, condition to produce an amphiphilic molecule or polymer. Polymers frequently adopt a random or disordered conformation in which the side chains are located randomly in space and there are no distinctive hydrophobic and hydrophilic regions.

The term "facially amphiphilic" or "facial amphiphilicity" as used herein describes polymers with polar (hydrophilic) and nonpolar (hydrophobic) side chains that adopt conformation(s) leading to segregation of polar and nonpolar side chains to opposite faces or separate regions of the structure. This structure can comprise any of the energetically accessible low-energy conformations for a given polymer backbone. Additionally random or block copolymers may adopt random backbone conformations that do not lead to distinct hydrophilic and hydrophobic regions or which do not segregate along different faces of the polymer. These copolymers are not facially amphiphilic as defined herein.

The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, carboxyglutamic acid, arginine, omithine and lysine. Unless specifically indicated, all amino acids referred to in this application are in the L-form.

The term "side chain of a naturally occurring amino acid" as used herein refers to the substituent on the a-carbon of a amino acid. The tern "polar side chain of a naturally occurring amino acid" refers to the side chain of a positively charged, negatively charged or hydrophilic amino acid. The term "nonpolar side chain of a naturally occurring amino acid" refers to the side chain of a hydrophobic amino acid.

The term "positively charged amino acid" or "cationic amino acid" as used herein includes any naturally occurring or unnatural amino acid having a positively charged side chain under normal physiological conditions. Examples of positively charged naturally occurring amino acids are arginine, lysine and histidine.

The term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

The term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

One embodiment of the present invention is a polymeric compound of formula I $$R^1 + x - A - y - x - B - y \overline{\smash{\Big)}_m} R^2 \qquad (I)$$

wherein:
x is $NR^3$, O, or S, y is C=O, C=S, O=S=O, or —C(=O)C(=O)— and $R^3$ is hydrogen, methyl or ethyl;

either both A and B are independently optionally substituted o-, m-, p-phenylene,
  or optionally substituted heteroarylene wherein (i) A and B are both substituted with a polar (P) group and a nonpolar (NP) group, (ii) one of A and B is substituted with a polar (P) group and a nonpolar (NP) group and the other of A and B is substituted with neither a polar nor a nonpolar group, or (iii) one of A or B is substituted with a polar (P) group and the other of A or B is substituted with a nonpolar (NP) group; or,
  one of A and B is o-, m-, p-phenylene or heteroarylene—the other of A and B is a $C_3$ to $C_8$ cycloalkyl or $(CH_2)_q$ where q is 1 to 7 wherein (i) one of A or B is optionally substituted by one or more polar (P) group(s) and the other of A or B is optionally substituted with one or more nonpolar (NP) group(s), or (ii) A is substituted with a polar (P) group and a nonpolar (NP) group and B is a $C_3$ to $C_8$ cycloalkyl or $(CH_2)_q$ where q is 1 to 7 and B is optionally independently substituted with one or more polar (P) or nonpolar (NP) group;

$R^1$ is (i) -y-C and $R^2$ is OH or $NH_2$ wherein C is selected from a group consisting of $C_1$–$C_6$ allcyl, vinyl, 2-propenyl, H-x-$(CH_2)_p$—, $(C_1$–$C_6$-alkoxy)C(=O) $(CH_2)_p$—, $C_1$–$C_6$ alkoxy, benzyloxy, t-butoxy, pyridine and phenyl said pyridine or phenyl optionally substituted with 1 or 2 substituents independently selected from a group consisting of halo, nitro, cyano, $C_1$–$C_6$ alkoxy, $C_1$–$C_6$ alkoxycarbonyl, and benzyloxycarbonyl; or, (ii) is H and $R^2$ is -x-$(CH_2)_p$—W wherein x is as defined above and p is as defined below and W is N-maleimide or V as defined below, or (iii) $R_1$ and $R_2$ together are a single bond;

NP is a nonpolar group an independently selected from $R^4$ or —U—$(CH_2)_p$—$R^4$ wherein $R^4$ is selected from a group consisting of hydrogen, $C_1$–$C_{10}$ alkyl, $C_3$–$C_{18}$ branched alkyl, $C_3$–$C_8$ cycloalkyl, monocyclic or polycyclic phenyl optionally substituted with one or more $C_1$–$C_4$ alkyl, $C_1$–$C_4$ alkoxy or halo groups and monocyclic or polycyclic heteroaryl optionally substituted with one or more $C_1$–$C_4$ alkyl, $C_1$–$C_4$ alkoxy, or halo groups and U and p are as defined below;

P is a polar group selected from a group consisting of IIIa, hydroxyethoxymethyl, methoxyethoxymethyl and polyoxyethylene $$-U-(CH_2)_p-V \qquad (IIIa)$$

wherein,
U is absent or selected from a group consisting of O, S, S(=O), S(=O)$_2$, NH, —C(=O)O—, —C(=O)NH—, —C(=O)S—, —C(=S)NH—, —S(=O)$_2$NH—, and C(=NO—) wherein groups with two chemically nonequivalent termini can adopt both possible orientations;

V is selected from a group consisting of amino, hydroxyl, thio, $C_1$–$C_6$ alkylamino, $C_1$–$C_6$ dialkylamino, $NH(CH_2)_pNH_2$, $N(CH_2CH_2NH_2)_2$, amidine, guanidine, semicarbazone, $C_1$–$C_6$ alkoxycarbonyl, basic heterocycle, and phenyl optionally substituted with an amino, $C_1$–$C_6$ alkylamino, $C_1$–$C_6$ dialkylamino and lower acylamnino optionally substituted with one or more amino, lower alkylamino or lower dialkylamino;

and the alkylene chain is optionally substituted with an amino or hydroxyl group or unsaturated;

p is independently 0 to 8;

m is 2 to at least about 500.

Another embodiment of polymer compound of formula VII:

(VII)

wherein
one of $R^9$ or $R^{10}$ and $R^{11}$ is a polar (P) group and the other of $R^9$ or $R^{10}$ and $R^{11}$ is a nonpolar (NP) group;

P is a polar group selected from a group consisting of IIIb, hydroxyethoxymethyl, methoxyethoxymethyl or polyoxyethylene $$-(CH_2)_p-V \qquad (IIIb)$$

wherein:
V is selected from a group consisting of amino, hydroxyl, $C_1$–$C_6$ allcylamino, $C_1$–$C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1$–$C_6$ alkylamino, $C_1$–$C_6$ dialkylamino and lower acylamino optionally substituted with one or more amino, lower alkylamino or lower dialkylamino; and, the alkylene chain is optionally substituted with an amino or hydroxyl group;

p is independently 0 to 8; and, m is 2 to at least about 30.

Still another embodiment of the present invention is a polyrneric compound of formula IX

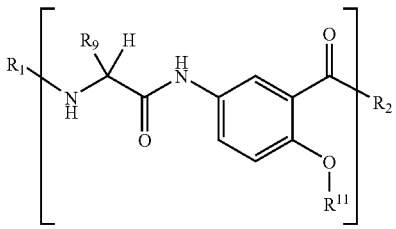

(IX)

wherein:
one of $R^9$ or $R^{11}$ is either a polar (P) group or a nonpolar (NP) group and the other of $R^9$ or $R^{11}$ is the other of a polar (P) group or a nonpolar (NP) group;

NP is $-(CH_2)_p-R^4$ wherein $R^4$ is selected from a group consisting of hydrogen, $C_1-C_4$ alkyl, $C_3-C_{12}$ branched alkyl, $C_3-C_8$ cycloalkyl, phenyl optionally substituted with one or more $C_1-C_4$ alkyl groups $C_1-C_4$ alkoxy or halo groups and heteroaryl optionally substituted with one or more $C_1-C_4$ alkyl group, $C_1-C_4$ alkoxy or halo groups and p is as defined below;

P is a polar group selected from a group consisting of IIIb, hydroxyethoxymethyl, methoxyethoxymethyl or polyoxyethylene

(IIIb)

wherein:
V is selected from a group consisting of amino, hydroxyl, $C_1-C_6$ alkylamino, $C_1-C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1-C_6$ alkylamino, $C_1-C_6$ dialkylamino and lower acylamino optionally substituted with one or more amino, lower alkylamino or lower dialkylamino; and, the alkylene chain is optionally substituted with an amino or hydroxyl group.

p is independently 0 to 8.

An embodiment of the present invention is a polymeric compound of formula IX wherein $R^9$ is a polar side chain of a natural amino acids and $R^{11}$ is selected from a group consisting of methyl, ethyl, n-propyl, iso-propyl, n-butyl iso-butyl, sec-butyl, tert-butyl, n-pentyl, iso-pentyl, sec-pentyl, and benzyl.

Another embodiment of the present invention is polymeric compound of formula IX wherein $R^9$ is a nonpolar side chain of a natural amino acids and $R^{11}$ is a polar group selected from a group consisting of IIIb, hydroxyethoxymethyl, methoxyethoxymethyl or polyoxyethylene

(IIIb)

wherein:
V is selected from a group consisting of amino, hydroxyl, $C_1-C_6$ alkylamino, $C_1-C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1-C_6$ alkylamino, $C_1-C_6$ dialkylamino and lower acylamino optionally substituted with one or more amino, lower alkylamino or lower dialkylamino; and, p is independently 0 to 8.

Still another embodiment of the present invention is a polymeric compound of formula I wherein:
x is NH and y is C=O or C=S;
A and B are independently optionally substituted o-, m-, or p-phenylene, 2,5-thiophenylene or 2,5-pyrrolene;
NP is a nonpolar group independently selected from $R^4$ or $-U-(CH_2)_p-R^4$ wherein $R^4$ is selected from a group consisting of hydrogen, $C_1-C_4$ alkyl, $C_3-C_{12}$ branched alkyl, $C_3-C_8$ cycloalkyl, phenyl optionally substituted with one or more $C_1-C_4$ alkyl groups $C_1-C_4$ alkoxy or halo groups and heteroaryl optionally substituted with one or more $C_1-C_4$ alkyl group, $C_1-C_4$ alkoxy or halo groups and U and p are as defined below;
P is a polar group selected from a group consisting of IIIa, hydroxyethoxymethyl, methoxyethoxymethyl or polyoxyethylene

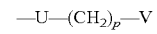

(IIIa)

wherein:
U is absent, O, S, SO, $SO_2$, or NH;
V is selected from a group consisting of amino, hydroxyl, $C_1-C_6$ alkylamino, $C_1-C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1-C_6$ alkylamino, $C_1-C_6$ dialkylamino and lower acylamino optionally substituted with one or more amino, lower alkylamino or lower dialkylamino; and,
the alkylene chain is optionally substituted with an amino or hydroxyl group;
p is independently 0 to 8; and,
m is 2 to at least about 500.

An embodiment of the present invention is a polymeric compound of formula I wherein:
x is $NR^3$, $R^3$ is hydrogen, and y is C=O or C=S;
A and B are independently optionally substituted o-, m-, or p-phenylene;
NP is a nonpolar group independently selected from $R^4$ or $-U-(CH_2)_p-R^4$ wherein $R^4$ is selected from a group consisting of hydrogen, methyl, ethyl, n-propyl, iso-propyl, n-butyl, iso-butyl, sec-butyl, tert-butyl, n-pentyl, iso-pentyl, and sec-pentyl and U and p are as defined below;
P is a polar group $U-(CH_2)_p-V$ wherein U is absent or selected from a group consisting of O and S, and V is selected from a group consisting of amino, lower alkyl amino, lower dialkylamino, imidazole, guanidine, $NH(CH_2)_pNH_2$, $N(CH_2CH_2NH_2)_2$, pyridine, piperidine, piperazine, 4-alkylpiperazine; and
p is independently 0 to 8;
m is 2 to at least about 500.

Another embodiment of the present invention is a polymeric compound of formula I wherein:
x is $NR^3$, y is CO, and $R^3$ is hydrogen;
A and B are m- or p-phenylene wherein (i) A is substituted at the 2-position with a polar (P) group and B is substituted at the 5-position with a nonpolar (NP) group, (ii) A is substituted at the 2-position with a polar (P) group and at the 5-position with a nonpolar (NP) group and B is substituted at the 2-position with a nonpolar (NP) group and at the 5-position with a polar (P) group or, (iii) A is substituted at the 2-position with one of a polar (P) or nonpolar (NP) group and B is substituted at the 2-position with the other of a nonpolar (NP) or a polar (P) group;

NP is a nonpolar group independently selected from $R^4$ or —U—$R^4$ wherein $R^4$ is selected from a group consisting of methyl, ethyl, n-propyl, iso-propyl, n-butyl, iso-butyl, sec-butyl, tert-butyl, n-pentyl, iso-pentyl, and sec-pentyl and U and p are as defined below;

p is independently 0 to 8; and, m is 2 to at least about 500.

Still another embodiment of the present invention is a polymeric compound of formula XII

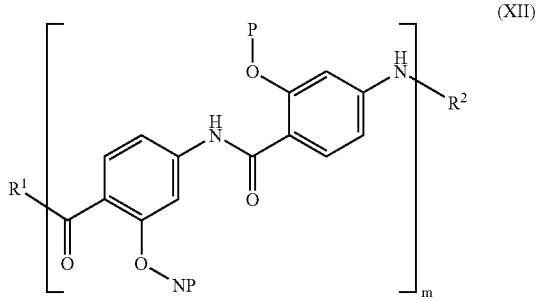

(XII)

wherein:
NP is a nonpolar group independently selected from a group consisting of methyl, ethyl, n-propyl, iso-propyl, n-butyl, iso-butyl, sec-butyl, tert-butyl, n-pentyl, iso-pentyl, and sec-pentyl and U and p are as defined below;

P is a polar group U—$(CH_2)_p$—V wherein U is selected from a group consisting of O, S, or no atom and V is selected from a group consisting of amino, lower alkyl amino, lower dialkylamino, imidazole, guanidine, $NH(CH_2)_pNH_2$, and $N(CH_2CH_2NH_2)_2$, piperidine, piperazine, 4-alkylpiperazine; and, p is independently 0 to 8;

m is 2 to at least about 30.

Yet another embodiment of the present invention is a polymer according to claim 8 comprising a compound of formula XIV,

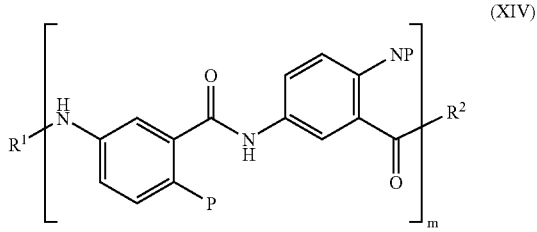

(XIV)

wherein:
NP is a nonpolar group independently selected from $R^4$ or —U—$R^4$ wherein $R^4$ is selected from a group consisting of methyl, ethyl, n-propyl, iso-propyl, 12-butyl, iso-butyl, sec-butyl, tert-butyl, n-pentyl, iso-pentyl, and sec-pentyl and U and p are as defined below;

P is a polar group U—$(CH_2)_p$—V wherein U is selected from a group consisting of O, S, or no atom and V is selected from a group consisting of amino, lower alkyl amino, lower dialkylamino, imidazole, guanidine, $NH(CH_2)_pNH_2$, and $N(CH_2CH_2NH_2)_2$, piperidine, piperazine, 4-alkylpiperazine; and, p is independently 0 to 8;

m is 2 to at least about 30.

Yet another embodiment of the present invention is a polymeric compound of formula I wherein:

x is $NR^3$, y is CO, and $R^3$ is hydrogen;

A and B are o-phenylene wherein A is substituted at the 5-position with a polar (P) group and B is substituted at the 5-position with a nonpolar (NP) group;

NP is a nonpolar group independently selected from $R^4$ or —U—$R^4$ wherein $R^4$ is selected from a group consisting of methyl, ethyl, n-propyl, iso-propyl, iso-butyl, n-butyl, sec-butyl, tert-butyl, n-pentyl, iso-pentyl, and sec-pentyl and U and p are as defined below;

P is a polar group U—$(CH_2)_p$—V wherein U is selected from a group consisting of O, S, or no atom and V is selected from a group consisting of amino, lower alkyl amino, lower dialkylamino, imidazole, guanidine, $NH(CH_2)_pNH_2$, and $N(CH_2CH_2NH_2)_2$, pyridine, piperidine, piperazine, 4-alkylpiperazine;

p is independently 0 to 8; and, m is 2 to at least about 500.

Another embodiment of the present invention is a polymeric compound of formula XIII:

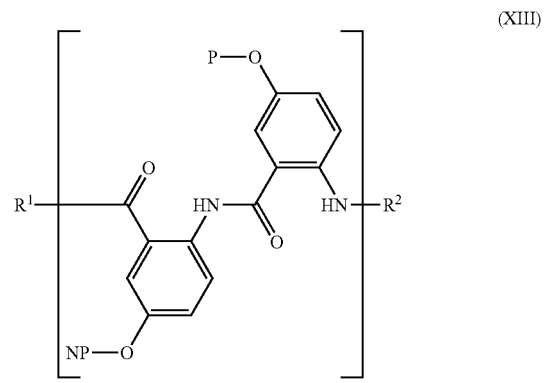

(XIII)

wherein:
NP is a nonpolar group independently selected from a the group consisting of methyl, ethyl, n-propyl, iso-propyl, n-butyl, iso-butyl, sec-butyl, tert-butyl, n-pentyl, iso-pentyl, and sec-pentyl and U and p are as defined below;

P is a polar group $(CH_2)_p$—V wherein V is selected from a group consisting of amino, lower alkyl amino, lower dialkylamino, guanidine, piperazine, 4-alkylpiperazine;

p is independently 0 to 8;

m is 2 to at least about 30.

An embodiment of the present invention is a polymeric compound of formula XV:

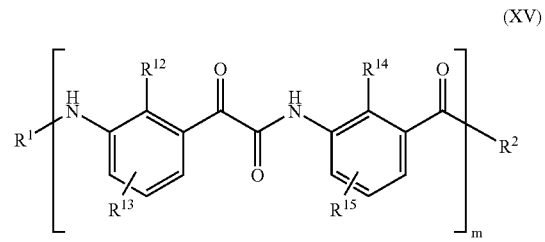

(XV)

wherein
- either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups
- NP is a nonpolar group independently selected from $R^4$ or —U—$R^4$ wherein $R^4$ is selected from a the group consisting of methyl, ethyl, n-propyl, iso-propyl, n-butyl, iso-butyl, sec-butyl, tert-butyl, n-pentyl, iso-pentyl, and sec-pentyl and U is defined below;
- P is a polar group U—$(CH_2)_p$—V wherein U is selected from a group consisting of O or S and V is selected from a group consisting of amino, lower alkyl amino, lower dialkylamino, guanidine, pyridine, piperazine, 4-alkylpiperazine;
- p is independently 0 to 8;
- m is 2 to at least about 30.

An embodiment of the present invention is a polymeric compound of formula II wherein:
- x and y can be (i) taken independently wherein x is $NR^3$, O, S, $(CR^7R^8)NR^3$, $(CR^7R^8)$, or $(CR^7R^8)S$, y is C=O, C=S, O=S=O, —C(=O)C(=O)—, $(CR^5R^6)C=O$ or $(CR^5R^6)C=S$, and $R^3$ is hydrogen, methyl or ethyl; or, (ii) taken together to be pyromellitic diimide; and $R^5$ and $R^6$ together are $(CH_2)_2NR^{12}(CH_2)_2$ and $R^{12}$ is selected from a group consisting of hydrogen —C(=N)$CH_3$ or C(=NH)—$NH_2$; and $R^7$ and $R^8$ together are $(CH_2)_p$ wherein p is as defined below;
- both A and B are independently optionally substituted o-, m-, p-phenylene, or optionally substituted heteroarylene wherein (i) A and B are both substituted with a polar (P) group and a nonpolar (NP) group, (ii) one of A and B is substituted with a polar (P) group and a nonpolar (NP) group and the other of A and B is substituted with neither a polar nor a nonpolar group, or (iii) one of A or B is substituted with a polar (P) group and the other of A or B is substituted with a nonpolar (NP) group;
- $R^1$ is (i) —B-y-$R^2$ and $R^2$ is -x-$(CH_2)_p$—W wherein x is as defined above and W is hydrogen, phenyl optionally substituted with up to three substituents selected from a group consisting of halogen, $C_1$–$C_4$ alkyl, $C_1$–$C_4$ alkoxy, and carboxyl, N-maleimide, or V as defined below, and p is an defined below; or, (ii) $R^1$ and $R^2$ together are a single bond
- NP is a nonpolar group an independently selected from $R^4$ or —U—$(CH_2)_p$—$R^4$ wherein $R^4$ is selected from a group consisting of hydrogen, $C_1$–$C_{10}$ alkyl, $C_3$–$C_{18}$ branched alkyl, $C_3$–$C_8$ cycloalkyl, monocyclic or polycyclic phenyl optionally substituted with one or more $C_1$–$C_4$ alkyl, $C_1$–$C_4$ alkoxy or halo groups and monocyclic or polycyclic heteroaryl optionally substituted with one or more $C_1$–$C_4$ alkyl, $C_1$–$C_4$ alkoxy, or halo groups and U and p are as defined below;
- P is a polar group selected from a group consisting of IIIa, hydroxyethoxymethyl, methoxyethoxymethyl and polyoxyethylene $$—U—(CH_2)_p—V \quad (IIIa)$$

wherein,
  - U is absent or selected from a group consisting of O, S, S(=O), S(=O)$_2$, NH, —C(=O)O—, —C(=O)NH—, —C(=O)S—, —C(=S)NH—, —S(=O)$_2$NH—, and C(=NO—) wherein groups with two chemically nonequivalent termini can adopt both possible orientations;
  - V is selected from a group consisting of amino, hydroxyl, thio, $C_1$–$C_6$ alkylamino, $C_1$–$C_6$ dialkylamino, NH$(CH_2)_p$NH$_2$, N$(CH_2CH_2NH_2)_2$, amidine, guanidine, semicarbazone, $C_1$–$C_6$ alkoxycarbonyl, basic heterocycle, and phenyl optionally substituted with an amino, $C_1$–$C_6$ alkylamino, $C_1$–$C_6$ dialkylamino and lower acylamino optionally substituted with one or more amino, lower alkylamino or lower dialkylamino;
  - and the alkylene chain is optionally substituted with an amino or hydroxyl group or unsaturated;
- p is independently 0 to 8;
- m is 2 to at least about 500.

Another embodiment of the present invention is a polymeric compound of formula II wherein:
- x=NH and y=CO;
- A and B are m- or p-phenylene wherein (i) A is substituted at the 2-position with a polar (P) group and B is substituted at the 5-position with a nonpolar (NP) group, or (ii) A is substituted at the 2-position with a polar (P) group and at the 5-position with a nonpolar (NP) group and B is either substituted at the 2-position with a nonpolar (NP) group and at the 5-position with a polar (P) group or B is unsubstituted;
- NP is a nonpolar group independently selected from $R^4$ or —U—$(CH_2)_p$—$R^4$ wherein $R^4$ is selected from a group consisting of methyl, ethyl, n-propyl, iso-propyl, iso-butyl, sec-butyl, tert-butyl, iso-pentyl, and sec-pentyl and U and p are as defined below;
- P is a polar group U—$(CH_2)_p$—V wherein U is absent or selected from a group consisting of O and S, and V is selected from a group consisting of amino, lower alkyl amino, lower dialkylamino, imidazole, guanidine, NH$(CH_2)_p$NH$_2$, N$(CH_2CH_2NH_2)_2$, piperidine, 4-alkylpiperazine and;
- p is independently 0 to 8;
- m is 2 to at least about 500.

Yet another embodiment of the present invention is a polymeric compound of formula II where A is an optionally substituted 1,3-diaminobenzene and B is an optionally substituted iso-phthalic acid.

Still another embodiment of the present invention is a polymeric compound of formula XI (XI)

wherein:
- $R^4$ is selected from a group consisting of methyl, ethyl, n-propyl, iso-propyl, n-butyl, iso-butyl, sec-butyl, tert-butyl, ii-pentyl, iso-pentyl, and sec-pentyl;
- U is O or S;
- V is amino, lower alkyl amino, lower dialkylamino, guanidine;

p is independently 0–8;

m is 2 to at least about 30.

Another embodiment of the present invention is a polymeric compound of formula XVI

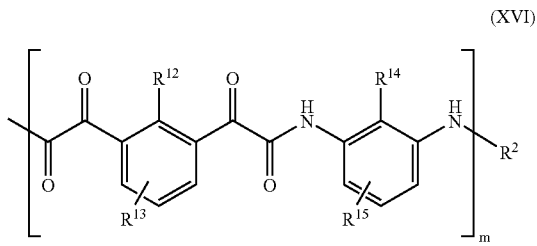

(XVI)

wherein:
either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups NP is a nonpolar group independently selected from $R^4$ or —U—$R^4$ where $R^4$ is selected from a group consisting of methyl, ethyl, n-propyl, iso-propyl, n-butyl, iso-butyl, sec-butyl, tert-butyl, n-pentyl, iso-pentyl, and sec-pentyl, and U is as defined below;

P is a polar group U—$(CH_2)_p$—V wherein U is absent or selected from a group consisting of O and S, and V is selected from a group consisting of amino, lower alkyl amino, lower dialkylamino, imidazole, guanidine, $NH(CH_2)_pNH_2$, $N(CH_2CH_2NH_2)_2$, piperidine, and 4-alkylpiperazine;

U is O or S;

V is amino, lower alkyl amino, lower dialkylamino, guanidine;

p is independently 0 to 8; and m is 2 to at least about 30.

Still another embodiment of the present invention is a polymeric compound of formula XX

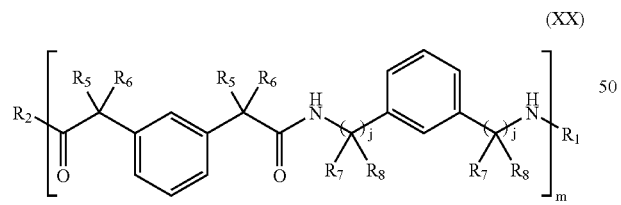

(XX)

wherein j is independently 0 or 1, $R^5$ and $R^6$ together are $(CH_2)_2NH(CH_2)_2$ and $R^7$ and $R^8$ together are $(CH_2)_p$ wherein p is 4 to 6.

Yet another embodiment of the present invention is a polymeric compound of formula IV

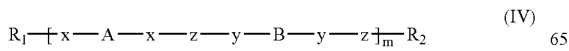

(IV)

wherein:
x is $NR^3$ or NHNH and y is $NR^3$, NHNH, S or O, and $R^3$ is hydrogen, methyl or ethyl;

z is C=O, —(C=O)C(=O)—, C=S or O=S=O;

A and B are independently optionally substituted o-, m-, p-phenylene or optionally substituted heteroarylene wherein (i) A and B are both substituted with a polar (P) group and a nonpolar (NP) group (NP), (ii) one of A and B is substituted with a polar (P) group and a nonpolar (NP) group and the other of A and B is substituted with neither a polar nor a nonpolar group, or (iii) one of A or B is substituted with one or two polar (P) group(s) and the other of A or B is substituted with one or two nonpolar (NP) group(s), or, or (iv) A is substituted at the 2-position with a polar (P) group and at the 5-position with a nonpolar (NP) group and B is unsubstituted;

$R^1$ is (i) —B-y-$R^2$ and $R^2$ is -x-$(CH_2)_p$—W wherein x is as defined above and W is hydrogen, pyridine and phenyl said pyridine or phenyl optionally substituted with 1 or 2 substituents independently selected from a group consisting of halo, nitro, cyano, $C_1$–$C_6$ alkoxy, $C_1$–$C_6$ alkoxycarbonyl, and benzyloxycarbonyl; $R^1$ is H and $R^2$ is -x-$(CH_2)_p$—V or (ii) $R_1$ and $R_2$ together are a single bond;

NP is a nonpolar group independently selected from $R^4$ or —U—$(CH_2)_p$—$R^4$ wherein $R^4$ is selected from a group consisting of $C_1$–$C_{18}$ alkyl, $C_3$–$C_{18}$ branched alkyl, $C_3$–$C_8$ cycloalkyl, monocyclic or polycyclic phenyl optionally substituted with one or more $C_1$–$C_4$ alkyl or halo groups, and monocyclic or polycyclic heteroaryl optionally substituted with one or more $C_1$–$C_4$ alkyl or halo groups and U and p are as defined below;

P is a polar group selected from a group consisting of IIIa, hydroxyethoxymethyl, methoxyethoxymethyl and polyoxyethylene

(IIIa)

wherein;
U is absent or selected from a group consisting of O, S, S(=O), $S(=O)_2$, NH, —C(=O)O—, —C(=O)NH—, —C(=O)S—, —C(=S)NH—, —$S(=O)_2$NH—, and C(=NO—) wherein groups with two chemically nonequivalent termini can adopt both possible orientations;

V is selected from a group consisting of amino, hydroxyl, $C_1$–$C_6$ alkylamino, $C_1$–$C_6$ dialkylamino, $NH(CH_2)_pNH_2$, $N(CH_2CH_2NH_2)_2$, amidine, guanidine, semicarbazone, basic heterocycle, and phenyl optionally substituted with an amino, $C_1$–$C_6$ alkylamino, $C_1$–$C_6$ dialkylamino and lower acylamino optionally substituted with one or more amino, lower alkylamino or lower dialkylamino;

and the alkylene chain is optionally substituted with an amino or hydroxyl group or optionally unsaturated;

p is independently 0 to 8;

m is 2 to at least about 500.

Yet another embodiment of the present invention is a polymeric compound of formula IV wherein:

x and y are $NR^3$, z is C=O or C=S, and $R^3$ is hydrogen;

A and B are independently optionally substituted o-, m-, or p-phenylene;

NP is a nonpolar group independently selected from $R^4$ or —U—$(CH_2)_p$—$R^4$ wherein $R^4$ is selected from a group consisting of hydrogen, $C_1$–$C_4$ alkyl, $C_3$–$C_{12}$ branched alkyl, $C_3$–$C_8$ cycloalkyl, phenyl optionally substituted with one or more $C_1$–$C_4$ alkyl groups and heteroaryl optionally substituted with one or more $C_1$–$C_4$ alkyl groups and U and p are as defined below;

P is a polar group selected from consisting of IIIa, hydroxyethoxymethyl, methoxyethoxymethyl or polyoxyethylene

wherein

U is O, S, S(=O), S(=O)$_2$, NH, or absent;

V is selected from a group consisting of amino, hydroxyl, $C_1$–$C_6$ alkylamino, $C_1$–$C_6$ dialkylamino, NH(CH$_2$)$_p$NH$_2$, N(CH$_2$CH$_2$NH$_2$)$_2$, amidine, guanidine, semicarbazone, and imidazole, piperidine, piperazine, 4-alkylpiperazine and phenyl optionally substituted with an amino, $C_1$–$C_6$ alkylamino, $C_1$–$C_6$ dialkylamino and lower acylamino optionally substituted with one or more amino, lower alkylamino or lower dialkcylamino;

and the alkylene chain is optionally substituted with an amino or hydroxyl group;

p is independently 0 to 8; and, m is 2 to at least about 500.

An embodiment of the present invention is a polymeric compound of formula IV wherein:

x and y are NH, z is C=O;

A and B are m- or p-phenylene and either (i) A is substituted at the 2-position with a polar (P) group and B is substituted at the 5-position with a nonpolar (NP) group, or (ii) A is substituted at the 5-position with a polar (P) group and B is substituted at the 2-position with a nonpolar (NP) group, or (iii) A and B are both substituted at the 2-position with a polar (P) group and at the 5-position with a nonpolar (NP) group, or (iv) A is substituted at the 2-position with a polar (P) group and at the 5-position with a nonpolar (NP) group and B is unsubstituted;

NP is a nonpolar group independently selected from $R^4$ or —U—(CH$_2$)$_p$—$R^4$ wherein $R^4$ is selected from a group consisting of hydrogen, methyl, ethyl, n-propyl, iso-propyl, iso-butyl, sec-butyl, tert-butyl, iso-pentyl, and sec-pentyl and U and p are as defined below;

P is a polar group U—(CH$_2$)$_p$—V wherein U is absent or selected from a group consisting of O, S and V is selected from a group consisting of amino, lower alkyl amino, lower dialkylamino, imidazole, guanidine, NH(CH$_2$)$_p$NH$_2$, and N(CH$_2$CH$_2$NH$_2$)$_2$, piperidine, piperazine, 4-alkylpiperazine;

p is independently 0 to 8; and, m is 2 to at least about 500.

Another embodiment of the present invention is a polymeric compound of formula XIV

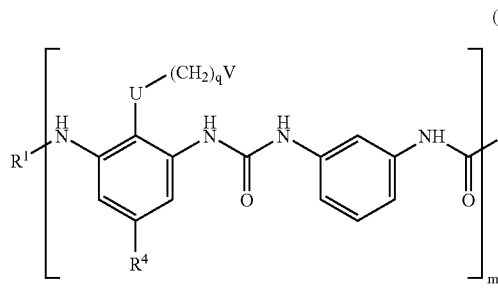

$R^4$ is selected from a group consisting of methyl, ethyl, n-propyl, iso-propyl, n-butyl, iso-butyl, sec-butyl, tert-butyl, n-pentyl, iso-pentyl, and sec-pentyl and U and p are as defined below;

U is absent, O or S and V is selected from a group consisting of amino, lower alkyl amino, lower dialkylamino, imidazole, guanidine, NH(CH$_2$)$_p$NH$_2$, and N(CH$_2$CH$_2$NH$_2$)$_2$, piperidine, piperazine, 4-alkylpiperazine; and, p is 0 to 8;

m is 2 to at least about 30.

Still another embodiment of the present invention is a polymeric compound of formula XVII

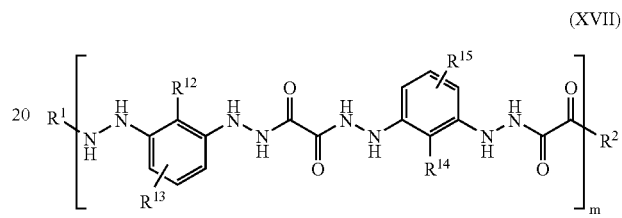

wherein:

either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups NP is a nonpolar group independently selected from $R^4$ or —U—$R^4$ wherein $R^4$ is selected from a the group consisting of methyl, ethyl, n-propyl, iso-propyl, n-butyl, iso-butyl, sec-butyl, tert-butyl, n-pentyl, iso-pentyl, and sec-pentyl and U and p are as defined below;

P is a polar group U—(CH$_2$)$_p$—V wherein U is selected from a group consisting of O or S and V is selected from a group consisting of amino, lower alkyl amino, lower dialkylamino, guanidine, pyridine, piperazine, 4-alkylpiperazine;

p is independently 0 to 8; and, m is 2 to at least about 30.

Another embodiment of the present invention is a polymeric compound of formula XVIII

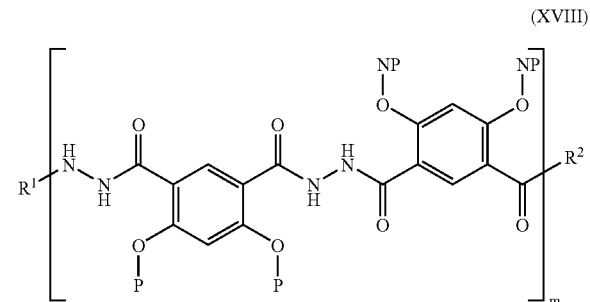

wherein:

NP is a nonpolar group independently selected from $R^4$ or —(CH$_2$)$_p$—$R^4$ wherein $R^4$ is selected from a group consisting of hydrogen methyl, ethyl, n-propyl, isopropyl, n-butyl, iso-butyl, sec-butyl, tert-butyl, n-pentyl, iso-pentyl, and sec-pentyl and p is as defined below;

P is a polar group $(CH_2)_p$—V wherein V is selected from a group consisting of amino, lower alkyl amino, lower dialkylamino, imidazole, guanidine, $NH(CH_2)_pNH_2$, and $N(CH_2CH_2NH_2)_2$, piperidine, piperazine, 4-alkylpiperazine;

p is independently 0 to 8; and, m is 2 to at least about 30.

Polyamides and polyesters that are useful for the present invention can be prepared by typical condensation polymerization and addition polymerization processes. [G. Odian, *Principles of Polymerization*, John Wiley & Sons, Third Edition (1991), M. Steven, *Polymer Chemistry*, Oxford University Press, (1999)] Most commonly the polyamides are prepared by (a) thermal dehydration of amine salts of carboxylic acids, (b) reaction of acid chlorides with amines and (c) aminolysis of esters. Methods (a) and (c) are of limited use in polymerizations of aniline derivatives which are generally prepared utilizing acid chlorides. The skilled chemist, however, will recognize that there are many alternative active acylating agents, for example phosphoryl anhydrides, active esters or azides, which may replace an acid chloride and which, depending on the particular polymer being prepared, may be superior to an acid chloride. The acid chloride route is probably the most versatile and has been used extensively for the synthesis of aromatic polyamides

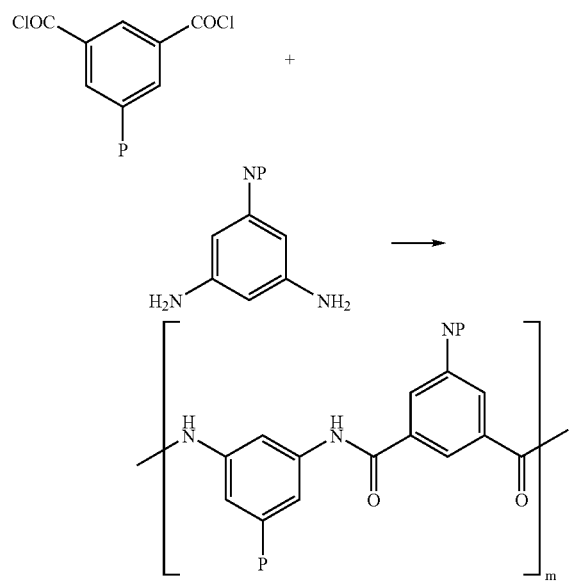

Homopolymers derived from substituted aminobenzoic acid derivatives (FIG. 1) can also prepared in a stepwise fashion. A stepwise process comprises coupling an N-protected amino acid to an amine (or hydroxy group) and subsequently removing the amine-protecting group and repeating the process. These techniques have been highly refined for synthesis of specific peptides, allow for the synthesis of specific sequences, and both solid-phase and solution techniques for peptide synthesis are directly applicable to the present invention. An alternative embodiment of the present invention is the corresponding polysulfonamides that can be prepared in analogous fashion by substituting sulfonyl chlorides for carboxylic acid chlorides.

The most common method for the preparation of polyureas is the reaction of diamines with diisocyanates. (Yamaguchi, I. et al. *Polym. Bull.* 2000 44, 247) This exothermic reaction can be carried out by solution techniques or by interfacial techniques. One skilled in organic and polymer chemistry will appreciate that the diisocyanate can be replaced with a variety of other bis-acylating agents e.g., phosgene or N, N'-(diimidazolyl)carbonyl, with similar results. Polyurethanes are prepared by comparable techniques using a diisocyanate and a dialcohol or by reaction of a diamine with a bis-chloroformate.

Figure 8:
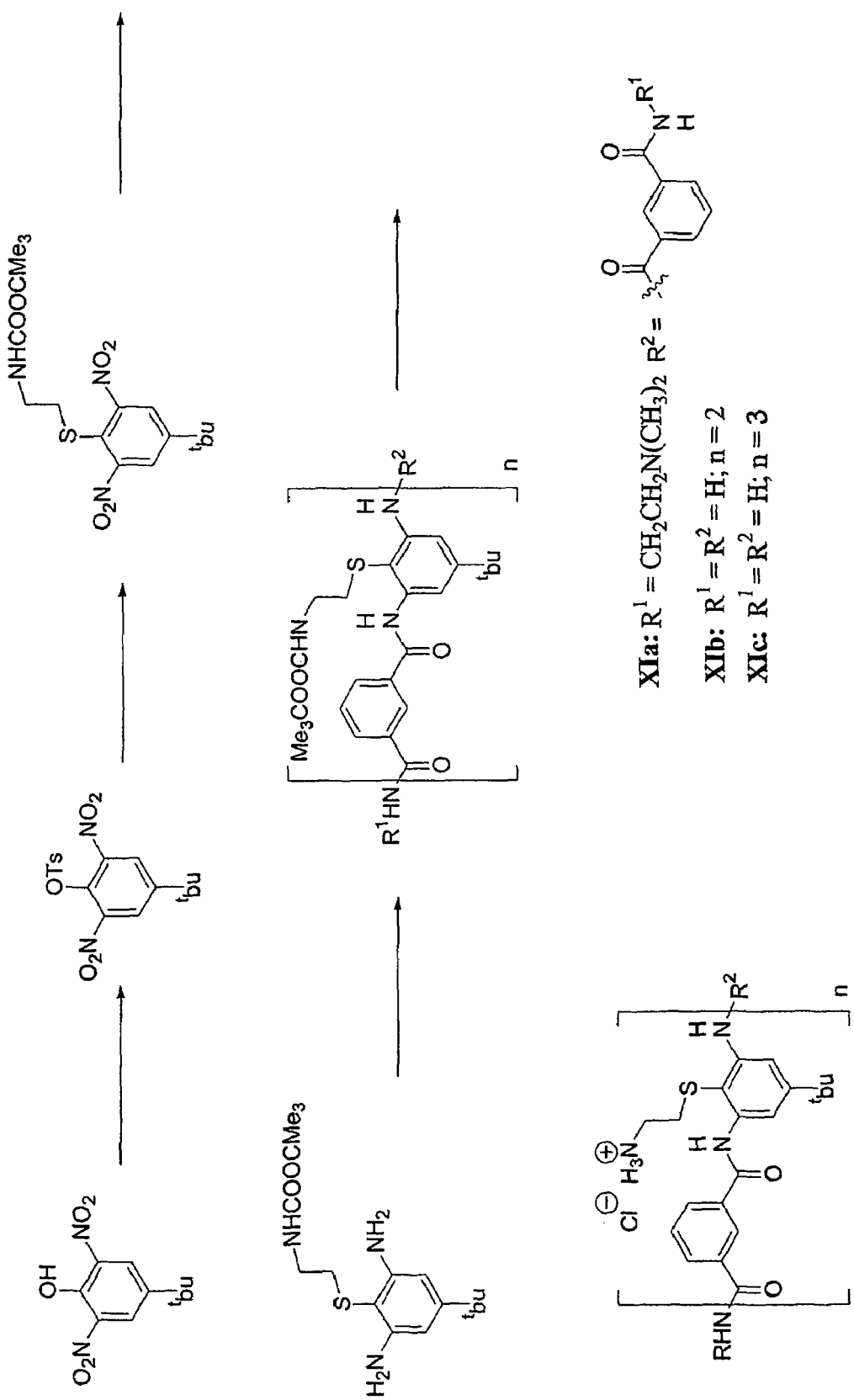
In FIG. 8 there is shown the synthesis of polyureas XIa–XIc.

The syntheses of appropriately substituted monomers are straightforward. Numerous pathways are available to incorporate of polar and nonpolar side chains. Phenolic groups on the monomer can be alkylated. Alkylation of the commercially available phenol will be accomplished with standard Williamson ether synthesis for the non-polar side chain with ethyl bromide as the alkylating agent. Polar sidechains can be introduced with bifunctional alkylating agents such as $BOC-NH(CH_2)_2Br$. Alternatively the phenol group can be alkylated to install the desired polar side chain function by employing Mitsonobu reaction with $BOC-NH(CH_2)_2$—OH, triphenyl phosphine, and diethyl acetylenedicarboxylate, Standard conditions for reduction of the nitro groups and hydrolysis of the ester afford the amino acid. With the aniline and benzoic acid in hand coupling can be effected under a variety of conditions. Alternatively the hydroxy group of the (di)nitrophenol can be converted to a leaving group and functionality introduced under nucleophilic aromatic substitution conditions (FIG. 8). Other potential scaffolds that can be prepare with similar sequences are methyl 2-nitro-4-hydroxybenzoate (FIG. 9) and methyl 2-hydroxy-4-nitrobenzoate.

Antimicrobial testing is carried out using the micro-broth dilution technique with *E. coli*. Other organisms screened include ampicillin & streptomycin-resistant *E. coli* D31, *B. subtilis*, vancomycin-resistant *Enterococcus faecium* A436, and methicillin-resistant *S. aureus* 5332. Any peptide that is found to be active will be purified to homogeneity, and retested to obtain an accurate $IC_{50}$. Secondary screens include *Klebsiella pneumoniae* Kp1, and *Salmonella typhimunium* S5, and *Pseudomonus aeruginosa* 10. Traditionally, the micro-broth dilution technique only evaluates a single data point between 18–24 hours; however, the measurements can be extended to 24 hr to monitor cell growth through the entire growth phase. These experiments are performed in LB medium (which is a rich medium typically used to grow cells for protein expression) and represent a critical initial screen for activity. Since salt concentrations, proteins, and other solutes can affect the activities of antibiotics, materials that showed no activity in rich medium were retested in minimal medium (M9) to determine if rich medium was limiting activity. No relationship between the media and the activity was observed which is consistent with the mode of action is believed to be through general membrane disruption.

To determine the toxicity to mammalian, as well to bacterial, cells the biocidal activity is evaluated using both cultured cells and freshly obtained human blood cells. Increasing concentration of polymer will be added to both confluent and non-confluent cultures of human umbilical endothelial cells (HUVEC, Cambrex). Cell number, monolayer integrity, and cell viability (measured as trypan blue exclusion) will be evaluated as a function of time in culture.

While the synthesis of a variety of polymer backbones is well understood, computer-aided computational techniques can provide valuable insight and guidance in the selection of potential antimicrobial polymers. The goal of these computations is to identify potential low energy conformations which have a geometrical repeat that matches a convenient sequence repeat of less than 6 monomer units. For example in α-amino acid oligomers, the geometrical repeat of the β-sheet is 2.0 residues. Once these repeating scaffolds are identified and the frequency of the repeat is calculated, polar and nonpolar substituents can be incorporated into the monomers to confer amphiphilic properties into the molecule.

High level ab initio calculations are one technique which will identify accessible low energy conformations. Unfortunately, these techniques, while extremely powerful, are not practical with molecules the size of the present invention. Molecular Dynamics simulations provide an alternative that can be adapted efficiently to molecules envisioned in the present invention. Key elements in determining conformational energies are strong electrostatic interactions (i.e., intramolecular hydrogen bonding) between adjacent or more distant monomers and rigidification caused by the backbone torsions or by bulky functional groups. In order to simulate these interactions in molecular mechanics calculations the empirical parameters, i.e., a force field, must be determined for representative polymer backbones. Density functional theory (DFT) can be used to carry out ab initio calculations on small model compounds that share the basic structural connectivity of the polymer backbones and which will generate required torsional potentials. The procedure to carry out these computations is:

1. Select simple model compounds that share similar torsional patterns with the target polymer backbones.
2. For each compound, perform a full geometric optimization at the BLYP/6–31G(d) level of theory (multiple initial configurations ensure the global minimum is obtained).
3. Calculate the single-point energy at the most stable geometry obtained in step 2 above, using B3LYP/6–311G++(dp) or plane wave CPMD.
4. Constrain a relevant torsion to a set angle and repeat steps 2 and 3.
5. Repeat step 4 for several angles; the torsional energy is obtained by subtracting the non-bonded interactions.
6. Fit energies versus torsion angle to a cosine series whose coefficients are the force field parameters.

After verifying the suitability of the force field by comparing computed predictions of the structure and thermodynamic properties to molecules that have similar torsional patterns and for which experimental data are available, the fitted torsions are then combined with bond stretching, bending, one-four, van der Waals, and electrostatic potentials borrowed from the CHARMM (B. R. Brooks et al. *J. Comp. Chem.* 1983 4:187–217 and TraPPE (M. G. Martin and J. I. Siepmann, *J. Phys. Chem B*. 1999 103:4508–17; C. D. Wick et al. *J. Phys. Chem B*. 2000 104:3093–3104) molecular dynamics force fields. To identify conformations that can adopt periodic folding patterns with polar groups and apolar groups lined up on the opposite sides. Initial structures can be obtained with the Gaussian package (M. Frisch et al. Gaussian 98 (revision A.7) Gaussian Inc., Pittsburgh, Pa. 1998). Then, the parallelized plane-wave Car-Parrinello CP-MD (R, Car and M. Parrinello *Phys. Rev. Lett.* 1985 55:2471–2474) program, (cf. U. Röthlisberger et al. *J. Chem. Phys.* 1996 3692–3700) is used to obtain energies at the minimum and constrained geometries. The conformations of the polymers without side-chains can be investigated in the gas phase. Both MD and MC methods will be used to sample the conformations. The former is useful for global motions of the polymer. With biasing techniques (J. I. Siepmann and D. Frenkel *Mol. Phys.* 1992 75:59–70; M. G. Martin and J. I. Siepmann *J. Phys. Chem. B* 1999 103:4508–4517; T. J. H. Vlugt et al. *Mol. Phys.* 1998 94:727–733) the latter allows efficient sampling for polymers with multiple local minimum configurations that are separated by relatively large barriers.

The potential conformations are examined for positions to attach pendant groups that will impart amphiphilic character to the secondary structure. Polymers selected from the gas-phase studies with suitable backbone conformations and with side-chains at the optimal positions to introduce amphiphilicity will be further evaluated in a model interfacial system, n-hexane/water, chosen because it is simple and cheap for calculations while it mimics well the lipid/water bilayer environment. Polymer secondary structures that require inter-polymer interactions can be identified by repeating the above-mentioned calculations using a periodically repeated series of unit cells of various symmetries (so called variable cell molecular dynamics or Monte Carlo technique) with or without solvent. The results of these calculations will guide the selection of candidates for synthesis.

An embodiment of the present is a computation technique to identify polymer backbones which can produce facially amphiphilic polymers by:
(1) selecting a polymer backbones or scaffolds suitable for regiospecific introduction of polar (P) and nonpolar (NP) groups;
(2) determining parameters for a molecular mechanics force field utilizing ab initio quantum mechanical calculations;
(3) calculating energetically accessible conformations of said backbone using molecular dynamics or molecular mechanics calculations;
(4) identifying energetically accessible conformations of said backbone wherein the periodicity of a geometrical/conformational repeat matches a sequence repeat;
(5) synthesizing monomers with polar and nonpolar substituents;
(6) synthesizing an antimicrobial polymer containing said monomers by solution or solid-phase synthesis.

The facially amphiphilic polymers of the present invention can have a substantial range in molecular weight. Facially amphiphilic molecules with molecular weights of about 0.8 kD to about 20 kD will be more prone to leach from the surface of the substrate. The facially amphiphilic polymer may be attached to, applied on or incorporated into almost any substrate including but not limited to woods, paper, synthetic polymers (plastics), natural and synthetic fibers, natural and synthetic rubbers, cloth, glasses and ceramics by appropriate methods including covalent bonding, ionic interaction, coulombic interaction, hydrogen bonding or cross-linking. Examples of synthetic polymers include elastically deformable polymers which may be thermosetting or thermoplastic including, but not limited to polypropylene, polyethylene, polyvinyl chloride, polyethylene terephthalate, polyurethane, polyesters, such as polylactide, polyglycolide, rubbers such as polyisoprene, polybutadiene or latex, polytetrafluoroethylene, polysulfone and polyethylenesulfone polymers or copolymers. Examples of natural fibers include cotton, wool and linen.

The polymers of the present invention thus provide a surface-mediated microbicide that only kills organisms in contact with the surface. Moreover the polymers of the present invention are stable and retain their bioactivity for extended periods of time. Polymers bound to the surface will not leach out of the surface into the environment. Specificity can be imparted for microbial cell walls which can provide polymers with reduced toxicity to birds, fish, mammals and other higher organisms.

Any object that is exposed to or susceptible to bacterial or microbial contamination can be treated with these polymers. These needs are particularly acute in the health care and food industries. A growing concern with preservatives has produced a need for new materials that prevent microbiological contamination without including preservatives. The incidence of infection from food-borne pathogens is a continuing concern and antimicrobial packaging material, utensils and surfaces would be valuable. In the health care and medical device areas the utility of antimicrobial instruments, packaging and surfaces are obvious. Products used internally or externally in humans or animal health including, but not limited to, surgical gloves, implanted devices, sutures, catheters, dialysis membranes, water filters and implements, all can harbor and transmit pathogens. The polymers of the present invention can be incorporated into spinnable fibers for use in materials susceptible to bacterial contamination including fabrics, surgical gowns, and carpets. Ophthalmic solutions and contact lenses easily become contaminated and cause ocular infections. Antimicrobial storage containers for contact lens and cleaning solutions would be very valuable. Both pets and agronomic animals are exposed to and harbor a variety of infectious pathogenic organisms that can cause disease in animals or humans.

Traditionally, monolayers have been created at air/water interfaces and transferred to a variety of surfaces for chemical and structural characterization, as documented in a large body of work dating back to the seminal studies of Blodgett and Langmuir. Monolayers can be chemically bonded to solid supports, resulting in stable, uniformly packed molecular layers that self-assemble by absorption. Typically, these Self-Assembled Monolayers (SAMS) are covalently tethered to solids using either alkylsiloxane or thiolate-gold linkages (for reviews see M. Mrksich, *Cell Mol Life Sci*, 1998 54:653–62; M. Mrksich, and G. M. Whitesides *Ann Rev Biophys Biomol Struct*, 1996 25:55–78). Alkylthiolate-gold linkages can be formed on the surface of gold by spontaneous absorption of a thiol or disulfide. Gold layers can be deposited on most solid surfaces, providing great versatility. Alkylsiloxane monolayers can be prepared by reacting trialkoxysilanes or trichlorosilanes with a silicon dioxide surface resulting in a monolayer of crosslinked siloxanes on the surface. Siloxane monolayers may be formed on any solid that contains surface silanol groups including atomically smooth, surface-oxidized silicon wafers, glass and quartz. These two chemistries will allow amphiphilic polymers to be attached a variety of surfaces.

These amphiphilic polymers can incorporate linkers to allow the polymers to more efficiently interact with the environment around the solid surface. Tethering chemistries that allow presentation of peptides and proteins in native conformations with minimal interaction with the underlying substrate have been described. For examples, alkanethiols of the general form, HS—$(CH_2)_{11}$—$(OCH_2$—$CH_2)_n$—OH (denoted HS—$C_{11}$-$E_n$, n=3–6), have now come into widespread use for studies of receptor/ligand interactions (M. Mrksich *Cell Mol. Life Sci*.1998 54:653–62; M. Mrksich and G. M. Whitesides *Ann. Rev. Biophys. Biomol. Struct*.1996 25:55–78). Polyethylene glycol derived amino acids, e.g. Fmoc-NH—$(CH_2$—$CH_2$—$O)_2)CH_2$—COOH (Neosystems) have also been described Cys will be appended to the N-terminus to act as a group that allows coupling via its thiol, directly or through chemoselective ligation (T. W. Muir et al. *Methods Enzymol*. 1997 289:266–98; G. G. Kochendoerfer et al. *Biochemistry* 1999 38:11905–13). The thiol group serves to tether the molecule to gold surfaces, while the terminal hydroxyl and ethylene glycol groups project towards solvent, presenting a hydrophilic surface. Attachment to siloxane and polyethylene surfaces have also been described. (S. P. Massia and J. Stark *J. Biomed. Mat. res.* 2001 56:390–9; S. P. Massia and J. A. Hubbell *J. Cell Biol.* 1991 114:1089–1100; S. P. Massia and J. A. Hubbell *Anal. Biochem.* 1990 187:292–301; B. T. Houseman and M. Mrksich *Biomaterials* 2001 22:943–55).

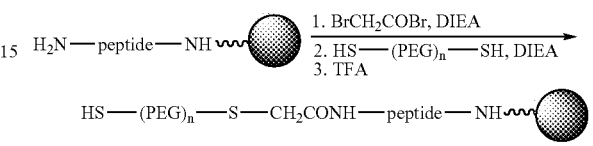

Resin bound intermediates can easily be modified to incorporate linkers. Glass surfaces can be modified to allow reaction with the thiol groups of the peptide by: (i) aminoalkylation of the glass surface by treatment with trimethoxysilylpropylamine; (ii) reaction of the amino groups with a bromoacetyl bromide or other heterobifunctional crosslinker groups capable of also reacting with a thiol group. In the above example, we show an amino surface in which we have introduced bromoacetyl groups for subsequent reaction with peptide thiols. Alternatively, thiol-reactive maleimides, vinyl-sulfones (Michael acceptors) may be incorporated using commercially available cross-linking agents. Alternatively, the surface amino groups may be converted to carboxylates by treatment with an anhydride, and then converted to thioesters under standard conditions. The resulting thioesters react facilely and with extreme regioselectivity with an N-terminal Cys residue. By incorporating quantities of inactive "filler" molecule, e.g. one example which is not limiting is a monofunctional thiol-terminated short chain polyethylene glycol polymer with the reactive teathering group the molar ratio of the oligomer to the "filler" component, it should be possible to continuously vary the surface density of the polymers attached to a solid support.

An embodiment of the present invention is a process for producing an antimicrobial surface by attaching a antimicrobial facially amphiphilic polymer to a surface comprising treating said surface with a first chemically reactive group and reacting a facially amphiphilic polymer linked to a second reactive group thereto.

Another embodiment of the present invention is a process for attaching a facially amphiphilic polymer to a surface wherein the solid surface is treated with a 1-(trialkoxysilyl) alkylamine and facially amphiphilic polymer contains an activated carboxylic acid.

Yet another embodiment of the present invention is a process for attaching a facially amphiphilic polymer to a surface wherein the solid surface is treated with a ω-(trialkoxysilyl)alkyl bromomethylacetamide and facially amphiphilic polymer contains a thiol.

Another embodiment of the present invention is a process for attaching a facially amphiphilic polymer to a surface wherein the solid surface is treated with a N-[ω-(trialkoxysilyl)alkyl]maleimide and facially amphiphilic polymer contains a thiol.

Still another embodiment of the present invention is a process for attaching a facially amphiphilic polymer to a surface wherein the surface is gold and the facially amphiphilic polymer contains a thiol.

A variety of polymers are used in a host of medical applications which require sterile surfaces. Catheters, like venous or urinary catheters are cause serious infections. Polyurethane based tubing is by far the major source of commercial catheter tubing. Amphiphilic polymers can be incorporated into polyurethane and other polymers using pre- and post manufacture techniques. The advantage of pre-manufacture incorporation is simpler modification strategies and dispersion of the antimicrobial agent throughout the tubing materials. Tubing manufacturing is typically an extrusion process in which pellets of polyurethane are heated and pressed through a dye producing tubing of the desired diameter. The thermal stability of urethane bonds is very similar to amide and urea bonds again suggesting that thermal processed conditions should not be a problem. For the pre-manufacture approach, designed antimicrobial polymers are added to the original polyurethane pellets before extrusion resulting in a uniform dispersion throughout the extruded polymer.

Post-manufacture modifications are also possible although in this case the antimicrobial polymer will only be present on the surface of the tubing. However, since catheters have a minimal life cycle it is likely that surface treatment will render the materials sufficiently sanitary for their application. There are a variety of methods one can use to modify polymeric surfaces (E. Piskin *J. Biomat. Sci.-Polymer Ed.* 1992 4:45–60). The most common technique to covalent attach a amphiphilic polymer to the surface relies on irradiation to produce free radicals that form covalent bonds between the polymer and active surface agent. Unfortunately, this process is completely random with no control over orientation or functional group attachment to the surface. Alternatively, photo or chemical oxidation of the polyurethane surface can create carboxylic acid or alcohol functionality which will be reactive toward these antimicrobial polymers (the cationic side chains or cationic end groups). The most common technique for surface oxidation is plasma etching (E. Piskin loc. cit.; S. H. Hsu and W. C. Chen, *Biomaterials* 2000 21:359–67) although ozone can also be used. After oxidation, the surface is treated with a bifunctional epoxide followed by addition of the cationic antimicrobial polymer which can react with the epoxide.

Microbial growth in paint and on the surface of paint films also remains an unsolved problem. This can occur in the wet formulated paint or by microbial growth on the dried surface. The paint industry currently uses either isothiazolones or "formaldehyde releasers" for wet paint protection from microbes (G. Sekaran et al. *J. Applied Polymer Sci.* 2001 81:1567–1571; T. J. Kelly et al. *Environ. Sci. Technol.* 1999 33:81–88; M. Sondossi et al. *International Biodeterioration & Biodegradation* 1993 32:243–61). Both of these products are harmful to human beings and great lengths and expense are taken at the factory to limit employee exposure; however, there is no viable alternative currently for the industry. Isothiazolones are used mainly for their effectiveness against *Pseudomonas aeruginosa* and that the antimicrobial polymers discussed in preliminary data are active against this strain.

Any object that is exposed to or susceptible to bacterial or microbial contamination can be treated with these polymers. These needs are particularly acute in the health care and food industries. A growing concern with preservatives has produced a need for new materials that prevent microbiological contamination without including preservatives. The incidence of infection from food-borne pathogens is a continuing concern and antimicrobial packaging material, utensils and surfaces would be valuable. In the health care and medical device areas the utility of antimicrobial instruments, packaging and surfaces are obvious. Products used internally or externally in humans or animal health including, but not limited to, surgical gloves, implanted devices, sutures, catheters, dialysis membranes, water filters and implements, all can harbor and transmit pathogens. The polymers of the present invention can be incorporated into spinnable fibers for use in materials susceptible to bacterial contamination including fabrics, surgical gowns, and carpets. Ophthalmic solutions and contact lenses easily become contaminated and cause ocular infections. Antimicrobial storage containers for contact lens and cleaning solutions would be very valuable. Both pets and agronomic animals are exposed to and harbor a variety of infectious pathogenic organisms that can cause disease in animals or humans.

An embodiment of the current invention is a antimicrobial composition comprising a facially amphiphilic polymer and a composition selected form the group consisting of paint, coatings, lacquer, varnish, caulk, grout, adhesives, resins, films, cosmetic, soap and detergent.

Another embodiment of the present invention is an improved catheter, the improvement comprising incorporating or attaching a facially amphiphilic polymer therein or thereto.

Yet another embodiment of the present invention is an improved contact lens, the improvement comprising incorporating or attaching an amphiphilic polymer therein or thereto.

An embodiment of the present invention is improved plastic devices for the hospital and laboratory the improvement comprising incorporating or attaching a facially amphiphilic polymer therein or thereto.

A further embodiment of the present invention is an improved woven and nonwoven fabrics for hospital use the improvement comprising the incorporating or attaching a facially amphiphilic polymer therein or thereto.

The following examples will serve to further typify the nature of this invention but should not be construed as a limitation in the scope thereof, which scope is defined solely by the appended claims.

EXAMPLE 1

Figure 6:
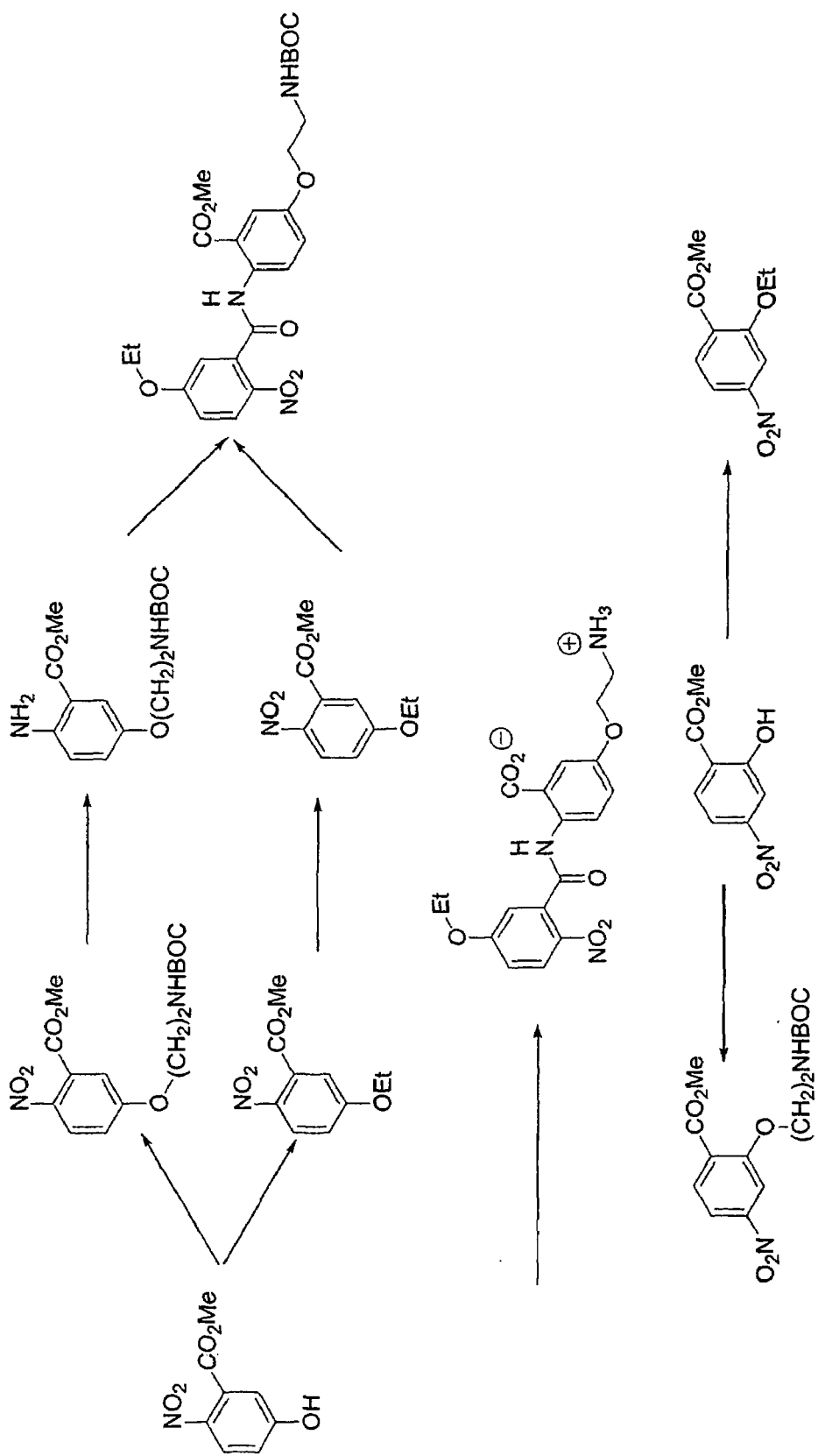
In FIG. 6 there is shown typical examples of ortho- and meta-phenylene facially amphiphilic polymers XII and XIII respectively derived from salicylamide and anthranilimide.

Polyamide FIG. 6 XIa 2,6-Dinitro-4-t-butyl-phenyl (4-methyl)-benzenesulfonate (11)

2,6-dinitro-4-t-butyl-phenol (80 mmol; 10) and tosyl chloride (80 mmol) were dissolved in 300 ml $CH_2Cl_2$. Diisopropylethylamine (DIEA, 80 mmol) was added to the solution. The mixture was stirred at room temperature for 2 hours. The solution was washed with 10% citric acid, saturated aqueous NaCl (sat. NaCl), and dried with $MgSO_4$. The solvent was removed under reduced pressure, and the product was obtained as a bright yellow solid in quantitative yield. $^1$H NMR (500 MHz, $CDCl_3$): δ=8.12 (s, 2H), 7.80 (d, 2H), 7.40 (d, 2H), 2.51(s, 3H), 1.41 (s, 9H). ESI-MS: m/z: 417.2 (M+Na$^+$).

2,6-Dinitro-4-t-butyl-1-(2-t-butoxycarbonylaminoethyl)-sulfanylbenzene (12).

Compound 11 (13 mmol), 2-Boc-aminoethanthiol (16 mmol) and DIEA(13 mmol) were dissolved in 50 ml chloroform. The solution was stirred under nitrogen for 12 hours. The solution was washed with 0.5 M NaOH, 10% citric acid, sat. Na$_2$CO$_3$ and sat. NaCl, and dried with MgSO$_4$. The solution volume was reduced to 15 ml by rotary evaporation. After addition of 80 ml hexane the product crystallized as a bright yellow solid in. 94% yield. $^1$H NMR (500 MHz, CDCl$_3$): δ 7.81 (s, 2H), 4.87 (s, 1H), 3.31 (t, 2H), 3.10 (t, 2H), 1.44 (s, 9H), 1.39 (s, 9H). ESI-MS: m/z: 422.4 (M+Na$^+$).

2,6-Diamino-4-t-butyl-1-(2-t-butoxycarbonylaminoethyl) sulfanylbenzene (13)

Dinitro compound 12 (20 mmol) and sodium acetate (200 mmol) were added to 50 ml EtOH. The mixture was heated to 78° C., and the solid dissolved completely. Stannous chloride dihydrate (200 mmol) was added to the solution, and the reaction mixture was stirred at 78° C. for 35 minutes. After removal of solvent under reduced pressure, the residue was dissolved in 800 ml EtOAc, and washed with 40% KCO$_3$. The organic phase was dried, evaporated and the residue column chromatographed (SiO$_2$) and eluted with a gradient of CH$_2$Cl$_2$/MeOH from 100:1 to 95:5 to produce 13 in 93% yield. $^1$H NMR (500 MHz, CDCl$_3$): δ 6.21 (s, 2H), 5.41 (s, 1H), 4.35 (br, 4H), 3.21 (t, 2H), 2.75 (t, 2H), 1.35 (s, 9H), 1.24 (s, 9H). ESI-MS: m/z: 340.5 (MH$^+$).

General Method of Polymerization.

Diamine 13 (0.1 mmol) was dissolved in 3 ml DMF. Isophthaloyl dichloride (0.1 mmol), triethylamine (0.2 mmol) ) and N,N-dimethylethylenediamine (0.2/n mmol) were added while stirring. The mixture was stirred under nitrogen for 18 hours. After the volume of solvent was reduced to 1 ml, water was added to precipitate the polymer. The polymer was collected and dried under vacuum. The Boc group was removed by treatment with trifluoroacetic acid (TFA, 3 ml) for 1 hour. The deprotected polymer was dried under vacuum overnight.

EXAMPLE 2

Solid Phase Synthesis of Oligomers XIb and XIc (FIG. 6)

Fmoc-PAL-PEG-resin (0.1 mmol) was swelled in DMF; then the Fmoc was removed with 20% piperidine in DMF for 20 min. The oligomer was then built up by alternately coupling 10 equivalents of isophthalic acid or diamine 10. In each case the couplings were carried out in DMF using 10 equivalents each of 2-(1H-benzotriazole-1-yl)-1,1,3,3,-tetramethyluronium hexafluorophosphate (HBTU) and N-hydroxybenzotriazole hydrate (HOBt), and 20 equivalents of DIEA for 24 hours at room temperature. The oligomers were cleaved from the resin by treatment with TFA/anisole (95:5) for 1 hour. Pure oligomers were obtained by HPLC on a reverse phase C4 column, with a linear gradient from 30% to 80% solvent B in 50 minutes (solvent A, 0.1% TFA in water; solvent B, acetonitrile/water/TFA 900:99:1). MALDI-TOF MS: XIb: 756.5 (M+H$^+$), XIc: 1125.6.(M+H$^+$).

EXAMPLE 3

General Method for Amide Polymerization

An oven-dried flask is charged with diamine dissolved in dimethylsulfoxide (DMSO). To this solution is added an equimolar quantity of the diacid chloride which is freshly prepared by stirring the dicarboxylic acid with excess thionyl chloride for 2 hr prior to addition to the diamine solution. A catalytic amount of 4-dimethylaminopyridine and four-fold molar excess of triethylamine are added to the stirring mixture. The reaction is stirred at room temperature overnight under positive N$_2$ pressure. The DMSO solution is poured into water and the solid polymer is recovered by filtration. The degree of polymerization is controlled by the addition of various molar amounts of a monofunctional amine. The molar amount of the monofunctional amine is determined by the Flory equation (G. Odian, *Principles of Polymerization*, John Wiley & Sons, Third Edition (1991) p.78–82).

EXAMPLE 4

General Method for Urea Polymerization

A dried flask is charged with equal molar ratios of the diamine and the diisocyanate in DMSO. The reaction is stirred at room temperature overnight under positive N$_2$ pressure. The reaction is poured into water or ether and the solid polymer is recovered by filtration. The degree of polymerization is controlled by the addition of various molar amounts of a monofunctional amine. The molar amount of the monofunctional amine is determined by the Flory equation.

EXAMPLE 5

Antimicrobial Assays

Figure 10:
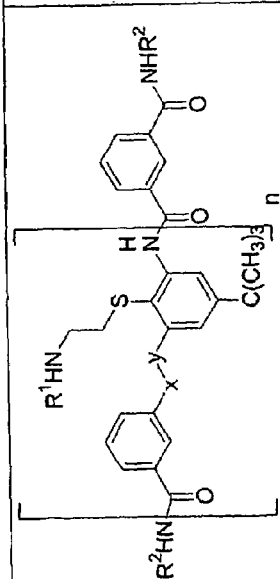

The inhibition studies will be carried out in suspension using BHI medium inoculated with bacteria (10$^6$ CFU/ml) in a 96-well format. A stock solution of the polymers was prepared DMSO/water and used to prepare a ten fold dilution series. Minimal inhibitory concentrations (MIC) were obtained by incubating the compounds with the bacteria for 18 hours at 37° C., and measuring cell growth by monitoring at 590 nm. Antibacterial data is described in FIGS. 10 and 11.

EXAMPLE 6

Hemolytic Activity

The toxicity of the polymers to mammalian cells was evaluated with human blood, anticoagulated with 0.1 volume of sodium citrate, obtained from healthy volunteers. Washed erythrocytes are suspended in either HEPES buffer, pH 7.4, containing 1 mM Mg$^{2+}$ and 1 mM Ca$^{2+}$ or in heated and unheated autologous serum obtained from clotted blood. Red cell agglutination will be evaluated microscopically and red cell lysis will be evaluated by measuring the amount of released hemoglobin spectroscopically. The effect of polymers on platelet function will be studied by adding increasing concentrations of polymer to citrate-anticoagulated platelet-rich plasma. Platelet aggregation and secretion will then be studied in a lumi-aggregometer (Chrono-Log).

All references cited in the application are hereby incorporated in their entirety into this specification. Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. Details of the structure may be varied substantially without departing from the spirit of the invention and the exclusive use of all modifications which come within the scope of the appended claim is reserved.

The invention claimed is:

1. A polymer or oligomer comprising a compound of formula I $$R^1 \!-\!\!\left[\!x\!-\!A\!-\!y\!-\!x\!-\!B\!-\!y\right]_m\!\!-\!R^2 \quad (I)$$

wherein:
- x is $NR^3$, O, or S; y is C=O, C=S, O=S=O, or —C(=O)C(=O)—; and $R^3$ is hydrogen, methyl or ethyl;
- either both A and B are independently optionally substituted o-, m-, p-phenylene, or optionally substituted heteroarylene wherein (i) A and B are both substituted with a polar (P) group and a nonpolar (NP) group, (ii) one of A and B is substituted with a polar (P) group and a nonpolar (NP) group and the other of A and B is substituted with neither a polar nor a nonpolar group, or (iii) one of A or B is substituted with a polar (P) group and the other of A or B is substituted with a nonpolar (NP) group; or,
- one of A and B is o-, m-, p-phenylene or heteroarylene and the other of A and B is a $C_3$ to $C_8$ cycloalkyl or $(CH_2)_q$ where q is 1 to 7 wherein (i) one of A or B is optionally substituted by one or more polar (P) group(s) and the other of A or B is optionally substituted with one or more nonpolar (NP) group(s), or (ii) A is substituted with a polar (P) group and a nonpolar (NP) group and B is a $C_3$ to $C_8$ cycloalkyl or $(CH_2)_q$ where q is 1 to 7 and B is optionally independently substituted with one or more polar (P) or nonpolar (NP) group;
- $R^1$ is (i) -y-C and $R^2$ is OH or $NH_2$ wherein C is selected from the group consisting of $C_1$–$C_6$ alkyl, $C_1$–$C_6$ haloalkyl, vinyl, 2-propenyl, H-x-$(CH_2)_p$—, $(C_1$–$C_6$-alkoxy)C(=O)$(CH_2)_p$—, $C_1$–$C_6$ alkoxy, benzyloxy, t-butoxy, pyridine and phenyl said pyridine or phenyl optionally substituted with 1 or 2 substituents independently selected from the group consisting of halo, nitro, cyano, $C_1$–$C_6$ alkoxy, $C_1$–$C_6$ alkoxycarbonyl, and benzyloxycarbonyl; or, (ii) is H and $R^2$ is -x-$(CH_2)_p$—W wherein x is as defined above and p is as defined below and W is H, N-maleimide or V as defined below, or (iii) -y-C and $R^2$ is -x-$(CH_2)_p$—W; or (iv) $R^1$ and $R^2$ together are a single bond;
- NP is a nonpolar group independently selected from $R^4$ or —U—$(CH_2)_p$—$R^4$ wherein $R^4$ is selected from the group consisting of hydrogen, $C_1$–$C_{10}$ alkyl, $C_1$–$C_6$ haloalkyl, $C_3$–$C_{18}$ branched alkyl, $C_3$–$C_8$ cycloalkyl, and monocyclic or polycyclic phenyl optionally substituted with one or more $C_1$–$C_4$ alkyl, $C_1$–$C_4$ alkoxy or halo groups and monocyclic or polycyclic heteroaryl optionally substituted with one or more $C_1$–$C_4$ alkyl, $C_1$–$C_4$ alkoxy, or halo groups and U and p are as defined below;
- P is a polar group selected from the group consisting of IIIa, hydroxyethoxymethyl, methoxyethoxymethyl and polyoxyethylene, $$—U—(CH_2)_p—V \quad (IIIa)$$

wherein:
- U is absent or selected from the group consisting of O, S, S(=O), S(=O)$_2$, NH, —C(=O)O—, —C(=O)NH—, —C(=O)S—, —C(=S)NH—, —S(=O)$_2$NH—, and C(=NO—) wherein groups with two chemically nonequivalent termini can adopt both possible orientations;
- V is selected from the group consisting of amino, hydroxyl, thio, $C_1$–$C_6$ alkylamino, $C_1$–$C_6$ dialkylamino, NH$(CH_2)_p$NH$_2$, N(CH$_2$CH$_2$NH$_2$)$_2$, amidine, guanidine, semicarbazone, $C_1$–$C_6$ alkoxycarbonyl, basic heterocycle, and phenyl optionally substituted with an amino, $C_1$–$C_6$ alkylamino, $C_1$–$C_6$ dialkylamino and lower acylamino optionally substituted with one or more amino, lower alkylamino or lower dialkylamino;
- and the alkylene chain is optionally substituted with an amino or hydroxyl group or unsaturated;
- p is independently 0 to 8; and
- m is 2 to at least about 500.

2. The polymer or oligomer of claim 1, wherein said polymer or oligomer comprises a compound of formula VII $$\left[\begin{array}{c} R^1 \diagdown \!\!\!\!\!\!\!\!\! \underset{H}{N} \!\!\!\!\!\! \diagup \!\!\!\!\!\!\!\!\!\underset{R^9\ R^{10}}{\phantom{X}} \!\!\!\!\!\!\!\!\!\!\!\! \diagdown \!\!\!\!\!\! \underset{O}{\overset{}{C}} \!\!\!\! \underset{H}{N} \cdots R^2 \\ R^{11} \end{array}\right]_m \quad (VII)$$

wherein:
- one of $R^9$ or $R^{10}$ and $R^{11}$ is a polar (P) group and the other of $R^9$ or $R^{10}$ and $R^{11}$ is a nonpolar (NP) group;
- P is a polar group selected from the group consisting of IIIb, hydroxyethoxymethyl, methoxyethoxymethyl and polyoxyethylene, $$—(CH_2)_p—V \quad (IIIb)$$

wherein:
- V is selected from the group consisting of amino, hydroxyl, $C_1$–$C_6$ alkylamino, $C_1$–$C_6$ dialkylamino, NH$(CH_2)_p$NH$_2$, N(CH$_2$CH$_2$NH$_2$)$_2$, amidine, guanidine, semicarbazone, imidazole, piperidine, piperazine, 4-alkylpiperazine and phenyl optionally substituted with an amino, $C_1$–$C_6$ alkylamino, $C_1$–$C_6$ dialkylamino and lower acylamino optionally substituted with one or more amino, lower alkylamino or lower dialkylamino; and,
- the alkylene chain is optionally substituted with an amino or hydroxyl group;
- p is independently 0 to 8; and
- m is 2 to at least about 30.

3. The polymer or oligomer of claim 2, wherein said polymer or oligomer comprises a compound of formula IX $$\left[\begin{array}{c} R^1 \diagdown \!\!\!\!\!\!\!\!\! \underset{H}{N} \!\!\!\!\!\! \diagup \!\!\!\!\!\!\!\!\!\underset{R^9\ H}{\phantom{X}} \!\!\!\!\!\!\!\!\!\!\!\! \diagdown \!\!\!\!\!\! \underset{O}{\overset{}{C}} \!\!\!\! \underset{H}{N} \cdots R^2 \\ R^{11} \end{array}\right] \quad (IX)$$

wherein:
one of $R^9$ or $R^{11}$ is either a polar (P) group or a nonpolar (NP) group and the other of $R^9$ or $R^{11}$ is the other of a polar (P) group or a nonpolar (NP) group;

NP is —$(CH_2)_p$—$R^4$ wherein $R^4$ is selected from the group consisting of hydrogen, $C_1$–$C_4$ alkyl, $C_3$–$C_{12}$ branched alkyl, $C_3$–$C_8$ cycloalkyl, and phenyl optionally substituted with one or more $C_1$–$C_4$ alkyl group, $C_1$–$C_4$ alkoxy or halo groups and heteroaryl optionally substituted with one or more $C_1$–$C_4$ alkyl group, $C_1$–$C_4$ alkoxy or halo groups and p is as defined below;

P is a polar group selected from the group consisting of IIIb, hydroxyethoxymethyl, methoxyethoxymethyl and polyoxyethylene, $$-(CH_2)_p-V \qquad (IIIb)$$

wherein:
V is selected from the group consisting of amino, hydroxyl, $C_1$–$C_6$ alkylamino, $C_1$–$C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1$–$C_6$ alkylamino, $C_1$–$C_6$ dialkylamino and lower acylamino optionally substituted with one or more amino, lower alkylamino or lower dialkylamino;

the alkylene chain is optionally substituted with an amino or hydroxyl group; and p is independently 0 to 8.

4. The polymer or oligomer of claim 3, wherein $R^9$ is a polar side chain of a natural amino acid and $R^{11}$ is selected from the group consisting of methyl, ethyl, n-propyl, iso-propyl, n-butyl iso-butyl, sec-butyl, tert-butyl, n-pentyl, iso-pentyl, sec-pentyl, and benzyl.

5. The polymer or oligomer of claim 3, wherein $R^9$ is a nonpolar side chain of a natural amino acid and $R^{11}$ is a polar group selected from the group consisting of IIIb, hydroxyethoxymethyl, methoxyethoxymethyl and polyoxyethylene, $$-(CH_2)_p-V \qquad (IIIb)$$

wherein:
V is selected from the group consisting of amino, hydroxyl, $C_1$–$C_6$ alkylamino, $C_1$–$C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1$–$C_6$ alkylamino, $C_1$–$C_6$ dialkylamino and lower acylamino optionally substituted with one or more amino, lower alkylamino or lower dialkylamino; and p is independently 0 to 8.

6. The polymer or oligomer of claim 1, wherein:
x is NH and y is C=O or CS;
A and B are independently optionally substituted o-, m-, or p-phenylene, 2,5-thiophenylene or 2,5-pyrrolene;
NP is a nonpolar group independently selected from $R^4$ or —U—$(CH_2)_p$—$R^4$ wherein $R^4$ is selected from the group consisting of hydrogen, $C_1$–$C_4$ alkyl, $C_3$–$C_{12}$ branched alkyl, $C_3$–$C_8$ cycloalkyl, phenyl optionally substituted with one or more $C_1$–$C_4$ alkyl groups, $C_1$–$C_4$ alkoxy or halo groups, and heteroaryl optionally substituted with one or more $C_1$–$C_4$ alkyl groups, $C_1$–$C_4$ alkoxy or halo groups, and U and p are as defined below;

P is a polar group selected from the group consisting of IIIa, hydroxyethoxymethyl, methoxyethoxymethyl and polyoxyethylene, $$-U-(CH_2)_p-V \qquad (IIIa)$$

wherein:
U is absent, O, S, SO, $SO_2$, or NH;
V is selected from the group consisting of amino, hydroxyl, $C_1$–$C_6$ alkylamino, $C_1$–$C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1$–$C_6$ alkylamino, $C_1$–$C_6$ dialkylamino and lower acylamino optionally substituted with one or more amino, lower alkylamino or lower dialkylamino; and, the alkylene chain is optionally substituted with an amino or hydroxyl group;

p is independently 0 to 8; and m is 2 to at least about 500.

7. The polymer or oligomer of claim 1, wherein:
x is $NR^3$, $R^3$ is hydrogen, and y is C=O or CS;
A and B are independently optionally substituted o-, m-, or p-phenylene;
NP a nonpolar group independently selected from R or —U—$(CH^2)_p$—$R^4$ wherein $R^4$ is selected from the group consisting of hydrogen, methyl, ethyl, n-propyl, iso-propyl, n-butyl, iso-butyl, sec-butyl, tert-butyl, n-pentyl, iso-pentyl, and sec-pentyl, and U and p are as defined below;

P is a polar group U—$(CH_2)_p$—V wherein U is absent or selected from the group consisting of O and S, and V is selected from the group consisting of amino, lower alkyl amino, lower dialkylamino, imidazole, guanidine, $NH(CH_2)_pNH_2$, $N(CH_2CH_2NH_2)_2$, pyridine, piperidine, piperazine, and 4-alkylpiperazine;

p is independently 0 to 8; and m is 2 to at least about 500.

8. The polymer or oligomer of claim 7, wherein:
x is $NR^3$, y is CO, and $R^3$ is hydrogen;
A and B are m- or p-phenylene wherein (i) A is substituted at the 2-position with a polar (P) group and B is substituted at the 5-position with a nonpolar (NP) group, (ii) A is substituted at the 2-position with a polar (P) group and at the 5-position with a nonpolar (NP) group and B is substituted at the 2-position with a nonpolar (NP) group and at the 5-position with a polar (P) group, or (iii) A is substituted at the 2-position with one of a polar (P) or nonpolar (NP) group and B is substituted at the 2-position with the other of a nonpolar (NP) or a polar (P) group;

NP is a nonpolar group independently selected from $R^4$ or —U—$R^4$ wherein $R^4$ is selected from the group consisting of methyl, ethyl, n-propyl, iso-propyl, n-butyl, iso-butyl, sec-butyl, tert-butyl, n-pentyl, iso-pentyl, and sec-pentyl, and U and p are as defined below;

p is independently 0 to 8; and m is 2 to at least about 500.

9. The polymer or oligomer of claim 8, wherein said polymer or oligomer comprises a compound of formula XII

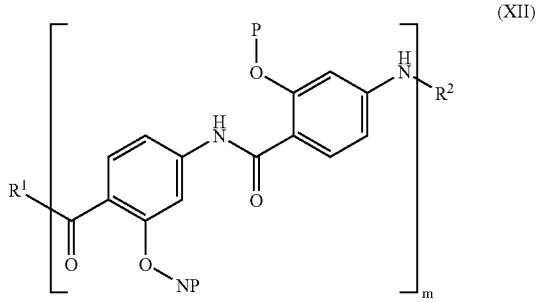

wherein:
NP is a nonpolar group independently selected from the group consisting of methyl, ethyl, n-propyl, iso-propyl, n-butyl, iso-butyl, sec-butyl, tert-butyl, n-pentyl, iso-pentyl, and sec-pentyl, and U and p are as defined below;

P is a polar group U—$(CH_2)_p$—V wherein U is selected from the group consisting of O, S, and no atom and V is selected from the group consisting of amino, lower alkyl amino, lower dialkylamino, imidazole, guanidine, $NH(CH_2)_pNH_2$, $N(CH_2CH_2NH_2)_2$, piperidine, piperazine, and 4-alkylpiperazine;

p is independently 0 to 8; and
m is 2 to at least about 30.

10. The polymer or oligomer of claim 8, wherein said polymer or oligomer comprises a compound of formula XIV,

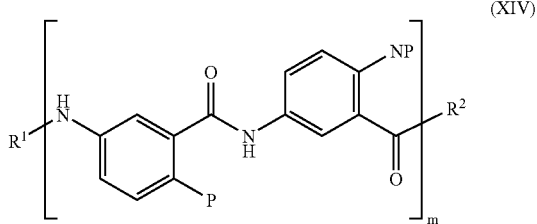

wherein:
NP is a nonpolar group independently selected from $R^4$ or —U—$R^4$ wherein $R^4$ is selected from the group consisting of methyl, ethyl, n-propyl, iso-propyl, n-butyl, iso-butyl, sec-butyl, tert-butyl, n-pentyl, iso-pentyl, and sec-pentyl, and U and p are as defined below;

P is a polar group U—$(CH_2)_p$—V wherein U is selected from the group consisting of O, S, and no atom and V is selected from the group consisting of amino, lower alkyl amino, lower dialkylamino, imidazole, guanidine, $NH(CH_2)_pNH_2$, $N(CH_2CH_2NH_2)_2$, piperidine, piperazine, and 4-alkylpiperazine;

p is independently 0 to 8; and
m is 2 to at least about 30.

11. The polymer or oligomer of claim 1, wherein:
x is $NR^3$, y is CO, and $R^3$ is hydrogen;
A and B are o-phenylene wherein A is substituted at the 5-position with a polar (P) group and B is substituted at the 5-position with a nonpolar (NP) group;
NP is a nonpolar group independently selected from $R^4$ or —U—$R^4$ wherein $R^4$ selected from the group consisting of methyl, ethyl, n-propyl, iso-propyl, iso-butyl, n-butyl, sec-butyl, tert-butyl, n-pentyl, iso-pentyl, and sec-pentyl, and U and p are as defined below;

P is a polar group U—$(CH_2)_p$—V wherein U is selected from the group consisting of O, S, and no atom and V is selected from the group consisting of amino, lower alkyl amino, lower dialkylamino, imidazole, guanidine, $NH(C_2)_pNH_2$, $N(CH_2CH_2NH_2)_2$, pyridine, piperidine, piperazine, and 4-alkylpiperazine;

p is independently 0 to 8; and
m is 2 to at least about 500.

12. The polymer or oligomer of claim 11, wherein said polymer or oligomer comprises a compound of formula XIII:

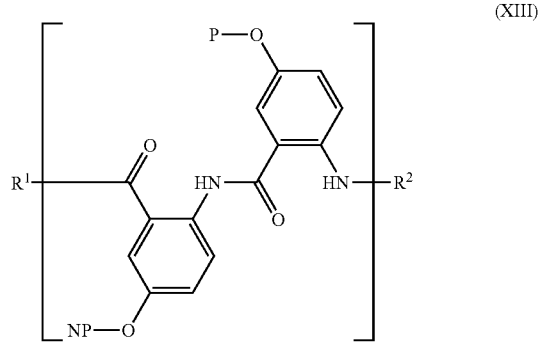

wherein:
NP is a nonpolar group independently selected from the group consisting of methyl, ethyl, n-propyl, iso-propyl, n-butyl, iso-butyl, sec-butyl, tert-butyl, n-pentyl, iso-pentyl, and sec-pentyl, and U and p are as defined below;

P is a polar group $(CH_2)_p$—V wherein V is selected from the group consisting of amino, lower alkyl amino, lower dialkylamino, guanidine, piperazine, and 4-alkylpiperazine;

p is independently 0 to 8; and
m is 2 to at least about 30.

13. The polymer or oligomer of claim 11, wherein said polymer or oligomer comprises a compound of formula XV:

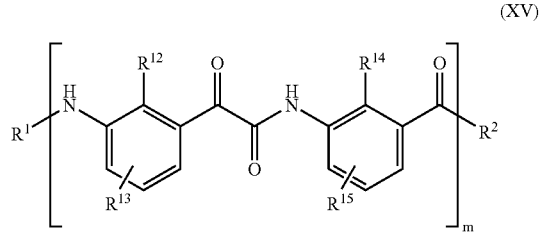

wherein
either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups;

NP is a nonpolar group independently selected from $R^4$ or —U—$R^4$ wherein $R^4$ is selected from the group consisting of methyl, ethyl, n-propyl, iso-propyl, n-butyl, iso-butyl, sec-butyl, tert-butyl, n-pentyl, iso-pentyl, and sec-pentyl, and U is defined below;

P is a polar group U—(CH$_2$)$_p$—V wherein U is selected from the group consisting of O and S and V is selected from the group consisting of amino, lower alkyl amino, lower dialkylamino, guanidine, pyridine, piperazine, and 4-alkylpiperazine;

p is independently 0 to 8; and m is 2 to at least about 30.

14. A polymer or oligomer comprising a compound of formula II

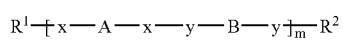
(II)

wherein:

x and y can be (i) taken independently wherein x is NR$^3$, O, S, (CR$^7$R$^8$)NR$^3$, (CR$^7$R$^8$)O, or (CR$^7$R$^8$)S, y is C=O, C=S, O=S=O, —C(=O)C(=O)—, (CR$^5$R$^6$)C=O or (CR$^5$R$^6$)C=S, and R$^3$ is hydrogen, methyl or ethyl; or, (ii) taken together to be pyromellitic diimide; and R$^5$ and R$^6$ together are (CH$_2$)$_2$NR$^{12}$(CH$_2$)$_2$ and R$^{12}$ is selected from the group consisting of hydrogen, C(=N)CH$_3$ and C(=NH)—N2 and R$^7$ and R$^8$ together are (CH$_2$)$_p$ wherein p is as defined below;

both A and B are independently optionally substituted o-, m-, p-phenylene, or optionally substituted heteroarylene wherein (i) A and B are both substituted with a polar (P) group and a nonpolar (NP) group, (ii) one of A and B is substituted with a polar (P) group and a nonpolar (NP) group and the other of A and B is substituted with neither a polar nor a nonpolar group, or (iii) one of A or B is substituted with a polar (P) group and the other of A or B is substituted with a nonpolar (NP) group;

R$^1$ is (i) -y-B-y-R$^2$ and R$^2$ is -x-(CH$_2$)$_p$—W, wherein x is as defined above and W is hydrogen, phenyl optionally substituted with up to three substituents selected from the group consisting of halogen, C$_1$–C$_4$ alkyl, C$_1$–C$_4$ alkoxy, and carboxyl, N-maleimide, or V as defined below, and p is as defined below; or, (ii) R$^1$ and R$^2$ together are a single bond;

NP is a nonpolar group an independently selected from R$^4$ or —U—(CH$_2$)$_p$—R$^4$ wherein R$^4$ is selected from the group consisting of hydrogen, C$_1$–C$_2$ alkyl, C$_1$–C$_6$ haloalkyl, C$_3$–C$_{18}$ branched alkyl, C$_3$–C$_8$ cycloalkyl, monocyclic or polycyclic phenyl optionally substituted with one or more C$_1$–C$_4$ alkyl, C$_1$–C$_4$ alkoxy or halo groups, and monocyclic or polycyclic heteroaryl optionally substituted with one or more C$_1$–C$_4$ alkyl, C$_1$–C$_4$ alkoxy, or halo groups, and U and p are as defined below;

P is a polar group selected from the group consisting of IIIa, hydroxyethoxymethyl, methoxyethoxymethyl and polyoxyethylene, —U—(CH$_2$)$_p$—V (IIIa)

wherein,

U is absent or selected from the group consisting of O, S, S(=O), S(=O)$_2$, NH, —C(=O)O—, —C(=O)NH—, —C(=O)S—, —C(S)NH—, —S(=O)$_2$NH—, and C(=NO—) wherein groups with two chemically nonequivalent termini can adopt both possible orientations;

V is selected from the group consisting of amino, hydroxyl, thio, C$_1$–C$_6$ alkylamino, C$_1$–C$_6$ dialkylamino, NH(CH$_2$)$_p$NH$_2$, N(CH$_2$CH$_2$NH$_2$)$_2$, amidine, guanidine, semicarbazone, C$_1$–C$_6$ alkoxycarbonyl, basic heterocycle, and phenyl optionally substituted with an amino, C$_1$–C$_6$ alkylamino, C$_1$–C$_6$ dialkylamino;

and lower acylamino optionally substituted with one or more amino, lower alkylamino or lower dialkylamino;

and the alkylene chain is optionally substituted with an amino or hydroxyl group or unsaturated;

p is independently 0 to 8; and m is 2 to at least about 500.

15. The polymer or oligomer of claim 14, wherein:

x=NH and y=CO;

A and B are m- or p-phenylene wherein (i) A is substituted at the 2-position with a polar (P) group and B is substituted at the 5-position with a nonpolar (NP) group, or (ii) A is substituted at the 2-position with a polar (P) group and at the 5-position with a nonpolar (NP) group and B is either substituted at the 2- position with a nonpolar (NP) group and at the 5-position with a polar (P) group or B is unsubstituted;

NP is a nonpolar group independently selected from R$^4$ or —U—(CH$_2$)$_p$—R$^4$ wherein R$^4$ is selected from the group consisting of methyl, ethyl, n-propyl, iso-propyl, iso-butyl, sec-butyl, tert-butyl, iso-pentyl, and sec-pentyl, and U and p are as defined below;

P is a polar group U—(CH$_2$)$_p$—V wherein U is absent or selected from the group consisting of O and S, and V is selected from the group consisting of amino, lower alkyl amino, lower dialkylamino, imidazole, guanidine, NH(CH$_2$)$_p$NH$_2$, N(CH$_2$CH$_2$NH$_2$)$_2$, piperidine, and 4-alkylpiperazine;

p is independently 0 to 8; and m is 2 to at least about 500.

16. The polymer or oligomer of claim 15, where A is an optionally substituted 1,3-diaminobenzene and B is an optionally substituted iso-phthalic acid.

17. The polymer or oligomer of claim 15, wherein said polymer or oligomer comprises a compound of formula XI

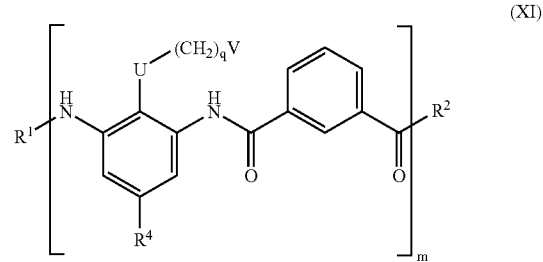
(XI)

wherein:

R$^4$ is selected from the group consisting of methyl, ethyl, n-propyl, iso-propyl, n-butyl, iso-butyl, sec-butyl, tert-butyl, n-pentyl, iso-pentyl, and sec-pentyl;

U is O or S;

V is amino, lower alkyl amino, lower dialkylamino, or guanidine;

p is independently 0–8; and m is 2 to at least about 30.

18. The polymer or oligomer of claim 15, wherein said polymer or oligomer comprises a compound of formula XVI

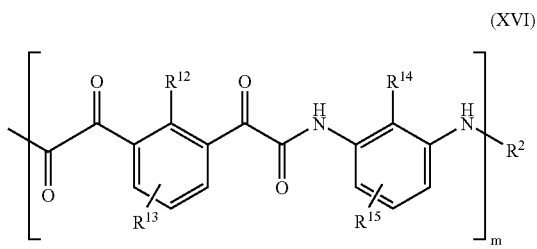

(XVI)

wherein:
either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups;

NP is a nonpolar group independently selected from $R^4$ or —U—$R^4$ where $R^4$ is selected from the group consisting of methyl, ethyl, n-propyl, iso-propyl, n-butyl, iso-butyl, sec-butyl, tert-butyl, n-pentyl, iso-pentyl, and sec-pentyl, and U is as defined below;

P is a polar group U—$(CH_2)_p$—V wherein U is absent or selected from the group consisting of O and S, and V is selected from the group consisting of amino, lower alkyl amino, lower dialkylamino, imidazole, guanidine, $NH(CH_2)_pNH_2$, $N(CH_2CH_2NH_2)_2$, piperidine, and 4-alkylpiperazine;

U is O or S;

V is amino, lower alkyl amino, lower dialkylamino, or guanidine;

p is independently 0 to 8; and m is 2 to at least about 30.

19. The polymer or oligomer of claim 15, wherein said polymer or oligomer comprises a compound of formula XX

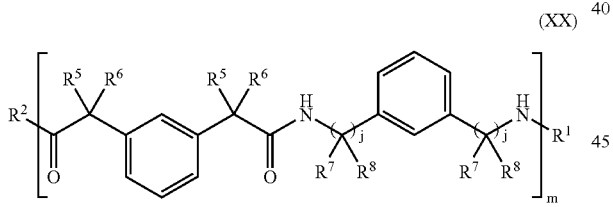

(XX)

wherein j is independently 0 or 1, $R^5$ and $R^6$ together are $(CH_2)_2NH(CH_2)_2$ and $R^7$ and $R^8$ together are $(CH_2)_p$ wherein p is 4 to 6.

20. A polymer or oligomer comprising a compound of formula IV

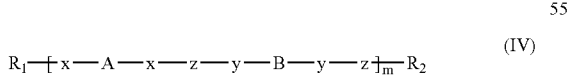

(IV)

wherein:
x is $NR^3$ or NHNH; y is $NR^3$, NHNH, S or O; and $R^3$ is hydrogen, methyl or ethyl;

z is C=O, —(C=O)C(=O)—, C=S or O=S=O;

A and B are independently optionally substituted o-, m-, p-phenylene or optionally substituted heteroarylene wherein (i) A and B are both substituted with a polar (P) group and a nonpolar (NP) group, (ii) one of A and B is substituted with a polar (P) group and a nonpolar (NP) group and the other of A and B is substituted with neither a polar nor a nonpolar group, (iii) one of A or B is substituted with one or two polar (P) group(s) and the other of A or B is substituted with one or two nonpolar (NP) group(s), or (iv) A is substituted at the 2-position with a polar (P) group and at the 5-position with a nonpolar (NP) group and B is unsubstituted;

$R^1$ is (i) —B-y-$R^2$ and $R^2$ is -x-$(CH_2)_p$—W wherein x is as defined above and W is hydrogen, pyridine and phenyl said pyridine or phenyl optionally substituted with 1 or 2 substituents independently selected from the group consisting of halo, nitro, cyano, $C_1$–$C_6$ alkoxy, $C_1$–$C_6$ alkoxycarbonyl, and benzyloxycarbonyl; (ii) $R^1$ is H and R is -x-$(CH_2)_p$—V, or (iii) $R^1$ and $R^2$ together are a single bond;

NP is a nonpolar group independently selected from $R^4$ or —U—$(CH_2)_p$—$R^4$ wherein $R^4$ is selected from the group consisting of $C_1$–$C_8$ alkyl, $C_1$–$C_6$ haloalkyl, $C_3$–$C_{18}$ branched alkyl, $C_3$–$C_8$ cycloalkyl, monocyclic or polycyclic phenyl optionally substituted with one or more $C_1$–$C_4$ alkyl or halo groups, and monocyclic or polycyclic heteroaryl optionally substituted with one or more $C_1$–$C_4$ alkyl or halo groups, and U and p are as defined below;

P is a polar group selected from the group consisting of IIIa, hydroxyethoxymethyl, methoxyethoxymethyl and polyoxyethylene,

—U—$(CH_2)_p$—V     (IIIa)

wherein:
U is absent or selected from the group consisting of O, S, S(=O), S(=O)$_2$, NH, —C(=O)O—, —C(=O)NH—, —C(=O)S—, —C(=S)NH—, —S(=O)$_2$NH—, and C(=NO—) wherein groups with two chemically nonequivalent termini can adopt both possible orientations;

V is selected from the group consisting of amino, hydroxyl, $C_1$–$C_6$ alkylamino, dialkylamino, $NH(CH_2)_pNH_2$, $N(CH_2CH_2NH_2)_2$, amidine, guanidine, semicarbazone, basic heterocycle, and phenyl optionally substituted with an amino, $C_1$–$C_6$ alkylamino, $C_1$–$C_6$ dialkylamino and lower acylamino optionally substituted with one or more amino, lower alkylamino or lower dialkylamino;

and the alkylene chain is optionally substituted with an amino or hydroxyl group or optionally unsaturated;

p is independently 0 to 8; and m is 2 to at least about 500.

21. The polymer or oligomer of claim 20, wherein:

x and y are $NR^3$, z is C=O or C=S, and $R^3$ is hydrogen;

A and B are independently optionally substituted o-, m-, or p-phenylene;

NP is a nonpolar group independently selected from $R^4$ or —U—$(CH_2)_p$—$R^4$ wherein $R^4$ is selected from the group consisting of hydrogen, $C_1$–$C_4$ alkyl, $C_3$–$C_{12}$ branched alkyl, $C_3$–$C_8$ cycloalkyl, phenyl optionally substituted with one or more $C_1$–$C_4$ alkyl groups and heteroaryl optionally substituted with one or more $C_1$–$C_4$ alkyl groups, and U and p are as defined below;

P is a polar group selected from the group consisting of IIIa, hydroxyethoxymethyl, methoxyethoxymethyl or polyoxyethylene,

—U—$(CH_2)_p$—V     (IIIa)

wherein:
U is O, S, S(=O), S(=O)$_2$, NH, or absent;

V is selected from a group consisting of amino, hydroxyl, $C_1$–$C_6$ alkylamino, dialkylamino, $NH(CH_2)_pNH_2$, $N(CH_2CH_2NH_2)_2$, amidine, guanidine, semicarbazone, and imidazole, piperidine, piperazine, 4-alkylpiperazine and phenyl optionally substituted with an amino, $C_1$–$C_5$ alkylamino, $C_1$–$C_6$ dialkylamino and lower acylamino optionally substituted with one or more amino, lower alkylamino or lower dialkylamino;

and the alkylene chain is optionally substituted with an amino or hydroxyl group;

p is independently 0 to 8; and, m is 2 to at least about 500.

22. The polymer or oligomer of claim 20, wherein:

x and y are NH, z is C=O;

A and B are m- or p-phenylene and either (i) A is substituted at the 2-position with a polar (P) group and B is substituted at the 5-position with a nonpolar (NP) group, or (ii) A is substituted at the 5-position with a polar (P) group and B is substituted at the 2-position with a nonpolar (NP) group, or (iii) A and B are both substituted at the 2-position with a polar (P) group and at the 5-position with a nonpolar (NP) group, or (iv) A is substituted at the 2-position with a polar (P) group and at the 5-position with a nonpolar (NP) group and B is unsubstituted;

NP is a nonpolar group independently selected from $R^4$ or —U—$(CH_2)_p$—$R^4$ wherein $R^4$ is selected from the group consisting of hydrogen, methyl, ethyl, n-propyl, iso-propyl, iso-butyl, sec-butyl, tert-butyl, iso-pentyl, and sec-pentyl, and U and p are as defined below;

P is a polar group U—$(CH_2)_p$—V wherein U is absent or selected from the group consisting of O and S and V is selected from the group consisting of amino, lower alkyl amino, lower dialkylamino, imidazole, guanidine, $NH(CH_2)_pNH_2$, $N(CH_2CH_2NH_2)_2$, piperidine, piperazine, and 4-alkylpiperazine;

p is independently 0 to 8; and m is 2 to at least about 500.

23. The polymer or oligomer of claim 20, wherein said polymer or oligomer comprises a compound of formula XIV

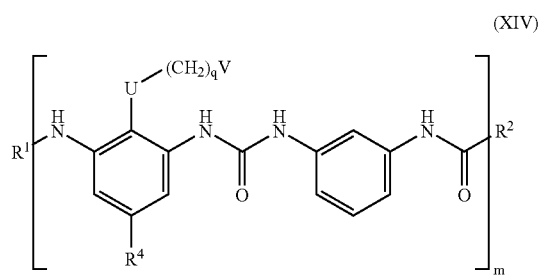

(XIV)

wherein:

$R^4$ is selected from the group consisting of methyl, ethyl, n-propyl, iso-propyl, n-butyl, iso-butyl, sec-butyl, tert-butyl, n-pentyl, iso-pentyl, and sec-pentyl, and U and p are as defined below;

U is absent, O or S and V is selected from the group consisting of amino, lower alkyl amino, lower dialkylamino, imidazole, guanidine, $NH(CH_2)_pNH_2$, $N(CH_2CH_2NH_2)_2$, piperidine, piperazine, and 4-alkylpiperazine;

p is 0 to 8; and m is 2 to at least about 30.

24. The polymer or oligomer of claim 20, wherein said polymer or oligomer comprises a compound of formula XVII

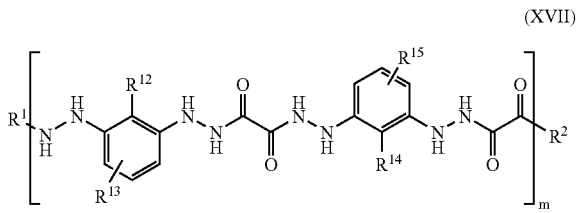

(XVII)

wherein:

either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups;

NP is a nonpolar group independently selected from $R^4$ or —U—$R^4$ wherein $R^4$ is selected from the group consisting of methyl, ethyl, n-propyl, iso-propyl, n-butyl, iso-butyl, sec-butyl, tert-butyl, n-pentyl, iso-pentyl, and sec-pentyl, and U and p are as defined below;

P is a polar group U—$(CH_2)_p$—V wherein U is selected from the group consisting of O and S and V is selected from the group consisting of amino, lower alkyl amino, lower dialkylamino, guanidine, pyridine, piperazine, and 4-alkylpiperazine;

p is independently 0 to 8; and m is 2 to at least about 30.

25. A polymer or oligomer comprising a compound of formula XVIII

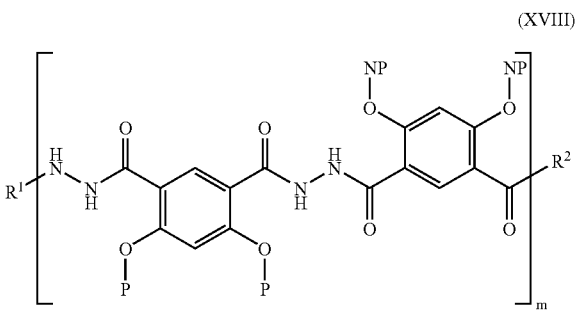

(XVIII)

wherein:

x=NH and y=CO;

$R^1$ is (i) -y-C and $R^2$ is OH or $NH_2$ wherein C is selected from the group consisting of $C_1$–$C_6$ alkyl, $C_1$–$C_6$ haloalkyl, vinyl, 2-propenyl, H-x-$(CH_2)_p$—, ($C_1$–$C_6$-alkoxy)C(=O)$(CH_2)_p$—, $C_1$–$C_6$ alkoxy, benzyloxy, t-butoxy, pyridine and phenyl said pyridine or phenyl optionally substituted with 1 or 2 substituents independently selected from the group consisting of halo, nitro, cyano, $C_1$–$C_6$ alkoxy, $C_1$–$C_6$ alkoxycarbonyl, and benzyloxycarbonyl; or, (ii) is H and $R^2$ is -x-$(CH_2)_p$—W wherein x is as defined above and p is as defined below and W is N-maleimide or V as defined below, or (iii) -y-C and $R^2$ is x$(CH_2)_p$—W; or (iv) $R^1$ and $R^2$ together are a single bond;

NP is a nonpolar group independently selected from $R^4$ or $-(CH_2)_p-R^4$ wherein $R^4$ is selected from the group consisting of hydrogen methyl, ethyl, n-propyl, isopropyl, n-butyl, iso-butyl, sec-butyl, tert-butyl, n-pentyl, iso-pentyl, sec-pentyl, and $C_1$–$C_5$-haloalkyl, and p is as defined below;

P is a polar group $(CH_2)_p$—V wherein V is selected from the group consisting of amino, lower alkyl amino, lower dialkylamino, imidazole, guanidine, $NH(CH_2)_p NH_2$, $N(CH_2CH_2NH_2)_2$, piperidine, piperazine, and 4-alkylpiperazine;

p is independently 0 to 8; and m is 2 to at least about 30.

26. A method of killing microorganisms, said method comprising the steps of:
Providing a substrate having disposed thereon a contact killing, facially amphiphilic polymer or oligomer of claim 1, claim 14, or claim 20;
Placing said facially amphiphilic polymer or oligomer disposed thereon on said substrate in contact with a microorganism to allow formation of pores in the cell wall of said microorganism.

27. The method of claim 26, wherein said substrate is selected from the group consisting of wood, synthetic polymers, plastics, natural and synthetic fibers, cloth, paper, rubber and glass.

28. The method of claim 27, wherein said substrate is from a plastic selected from the group consisting of polysulfone, polyacrylate, polyurea, polyethersulfone, polyamide, polycarbonate, polyvinylidenefluoride, polyethylene, polypropylene and cellulosics.

29. A microbiocidal composition comprising a facially amphiphilic polymer or oligomer of claim 1, claim 14, or claim 20 and a solid support selected from the group consisting of wood, synthetic polymers, natural and synthetic fibers, cloth, paper, rubber and glass.

30. The microbiocidal composition of claim 29, wherein said solid support is a plastic selected from the group consisting of polysulfone, polyacrylate, polyethersulfone, polyamide, polycarbonate, polyvinylidenefluoride, polyethylene, polypropylene and cellulosics.

31. A method for identifying a facially amphiphilic polymer or oligomer of claim 1, claim 14, or claim 20, said method comprising:
(1) selecting a polymer or oligomer backbone or scaffold in which polar (P) and nonpolar (NP) groups can be incorporated;
(2) determining parameters for a molecular mechanics force field utilizing ab initio quantum mechanical calculations;
(3) calculating energetically accessible conformations of said backbone using molecular dynamics or molecular mechanics calculations;
(4) identifying energetically accessible conformations of said backbone wherein the periodicity of a geometrical/conformational repeat matches a sequence repeat;
(5) synthesizing monomers with polar and nonpolar substituents;
(6) synthesizing an antimicrobial polymer or oligomer containing said monomers by solution or solid-phase synthesis.

32. A process for producing an antimicrobial surface by attaching an antimicrobial facially amphiphilic polymer or oligomer of claim 1, claim 14, or claim 20 to a surface, said process comprising treating said surface with a first chemically reactive group and reacting said polymer or oligomer linked to a second reactive group thereto.

33. The process of claim 32, wherein said first reactive group is a 1-(trialkoxysilyl)propylamine and said second reactive group is an activated carboxylic acid.

34. The process of claim 32, wherein said first reactive group is a ω-(trialkoxysilyl)alkyl bromomethylacetamide and said second reactive group is a thiol.

35. The process of claim 32, wherein said first reactive group is a N-[ω-(trialkoxysilyl)alkyl] maleimide and said second reactive group is a thiol.

36. The process of claim 32, wherein said first reactive group is a gold surface and said second reactive group is a thiol.

37. An antimicrobial composition comprising a facially amphiphilic polymer or oligomer of claim 1, claim 14, or claim 20 and a composition selected from the group consisting of paint, coatings, lacquer, varnish, caulk, grout, adhesives, resins, films, cosmetics, soap and detergent.

38. An improved catheter, said improvement comprising incorporating or attaching an antimicrobial facially amphiphilic polymer or oligomer of claim 1, claim 14, or claim 20 therein or thereto.

39. An improved contact lens, said improvement comprising incorporating or attaching an antimicrobial facially amphiphilic polymer or oligomer of claim 1, claim 14, or claim 20 therein or thereto.

40. An improved plastic device for the hospital and laboratory, said improvement comprising incorporating or attaching an antimicrobial facially amphiphilic polymer or oligomer of claim 1, claim 14, or claim 20 therein or thereto.

41. An improved woven and nonwoven fabric for hospital use, said improvement comprising incorporating or attaching an antimicrobial facially amphiphilic polymer or oligomer of claim 1, claim 14, or claim 20 therein or thereto.

42. A microbiocidal composition comprising a facially amphiphilic polymer or oligomer of claim 1, claim 14, or claim 20 and a medical device or medical product.

43. The microbiocidal composition of claim 42, wherein the medical device or medical product is selected from the group consisting of surgical gloves, implanted devices, sutures, catheters, dialysis membranes, and water filters and implements.

44. A microbiocidal composition comprising a facially amphiphilic polymer or oligomer of claim 1, claim 14, or claim 20 and a material comprising spinnable fibers.

45. The microbiocial composition of claim 44, wherein the material comprising spinnable fibers is selected from the group consisting of fabrics, surgical gowns, and carpets.

\* \* \* \* \*

UNITED STATES PATENT AND TRADEMARK OFFICE
CERTIFICATE OF CORRECTION

PATENT NO.       : 7,173,102 B2
APPLICATION NO.  : 10/471028
DATED            : February 6, 2007
INVENTOR(S)      : DeGrado et al.

It is certified that error appears in the above-identified patent and that said Letters Patent is hereby corrected as shown below:

In claim 7, column 36, line 28, please delete "NP a nonpolar group independently selected from R or" and insert therein -- NP a nonpolar group independently selected from $R^4$ or --.

In claim 14, column 39, line 26, please delete "C(=NH)—N2" and insert therein -- C(=NH)—$NH_2$ --.

In claim 14, column 40, lines 6-8, please delete "dialkylamino; and lower acylamino optionally" and insert therein -- dialkylamino and lower acylamino optionally --.

In claim 17, column 40, lines 46 to 54, please delete

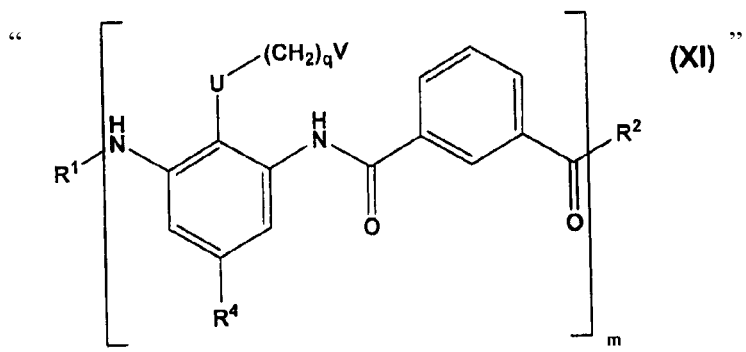

and insert therein

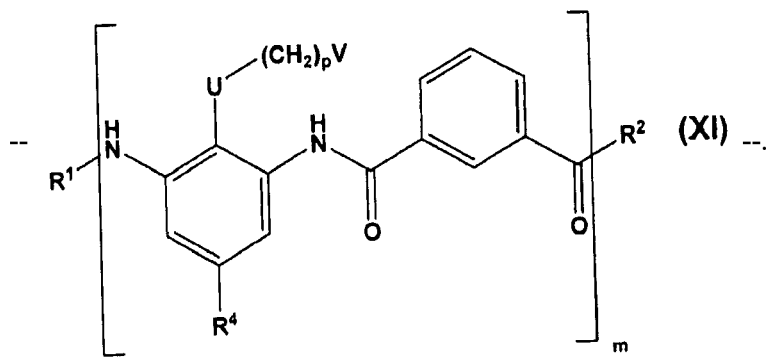

UNITED STATES PATENT AND TRADEMARK OFFICE
CERTIFICATE OF CORRECTION

PATENT NO. : 7,173,102 B2
APPLICATION NO. : 10/471028
DATED : February 6, 2007
INVENTOR(S) : DeGrado et al.

It is certified that error appears in the above-identified patent and that said Letters Patent is hereby corrected as shown below:

In claim 20, column 41, lines 56 to 58, please delete and insert therein

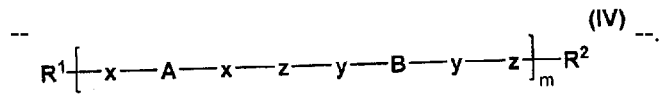

In claim 20, column 42, line 7, please delete "$_2$-position" and insert therein -- 2-position --.

In claim 20, column 42, lines 14-15, please delete "(ii) $R^1$ is $^1H$ and R is -x-($CH_2$)$_P$-V," and insert therein -- (ii) $R^1$ is H and $R^2$ is -x-($CH_2$)$_P$-V, --.

In claim 25, column 44, line 66, please delete "-y-C and $R^2$ is x($CH_2$)$_P$—W;" and insert therein -- -y-C and $R^2$ is -x-($CH_2$)$_P$—W; --.

Signed and Sealed this

Fifteenth Day of July, 2008

JON W. DUDAS
*Director of the United States Patent and Trademark Office*